(12) United States Patent
Yarden et al.

(10) Patent No.: US 9,415,103 B2
(45) Date of Patent: Aug. 16, 2016

(54) COMBINATION THERAPY TO PREVENT DCIS FORMATION AND PROGRESSION TO BREAST CANCER

(75) Inventors: Yosef Yarden, Rehovot (IL); Pradeep Chaluvally-Raghavan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 9 days.

(21) Appl. No.: 14/125,588

(22) PCT Filed: Jun. 14, 2012

(86) PCT No.: PCT/IL2012/050207
§ 371 (c)(1),
(2), (4) Date: Dec. 12, 2013

(87) PCT Pub. No.: WO2012/172555
PCT Pub. Date: Dec. 20, 2012

(65) Prior Publication Data
US 2014/0356350 A1    Dec. 4, 2014

Related U.S. Application Data

(60) Provisional application No. 61/496,577, filed on Jun. 14, 2011.

(51) Int. Cl.
| | |
|---|---|
| *A61K 31/506* | (2006.01) |
| *A61K 31/713* | (2006.01) |
| *A61K 31/7088* | (2006.01) |
| *A61K 39/395* | (2006.01) |
| *A61K 45/06* | (2006.01) |
| *C12Q 1/68* | (2006.01) |
| *G01N 33/574* | (2006.01) |
| *C12N 15/113* | (2010.01) |
| *C07K 16/32* | (2006.01) |
| *A61K 31/517* | (2006.01) |
| *C07K 16/22* | (2006.01) |
| *C07K 16/28* | (2006.01) |

(52) U.S. Cl.
CPC ........... *A61K 39/3955* (2013.01); *A61K 31/506* (2013.01); *A61K 31/517* (2013.01); *A61K 31/7088* (2013.01); *A61K 31/713* (2013.01); *A61K 39/39558* (2013.01); *A61K 45/06* (2013.01); *C07K 16/32* (2013.01); *C12Q 1/6886* (2013.01); *G01N 33/57415* (2013.01); *C12N 15/113* (2013.01); *C12N 15/1135* (2013.01); *C12N 15/1138* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

2009/0137470 A1* 5/2009 Stylianou .................. 514/12

FOREIGN PATENT DOCUMENTS

| WO | WO 2010/021729 | 2/2010 |
| WO | WO 2012/172555 | 12/2012 |

OTHER PUBLICATIONS

Capaccione et al. The Notch signaling pathway as a mediator of tumor surivival. Carcinogenesis 34(7): 1420-1430, 2013.*
Freudenberg et al. The role of HER2 in early breast cancer metastasis and the origins of resistance to HER2-targeted therapies. Exp Mol Pathol 87: 1-11, 2009.*
Geyer et al. Lapatinib plus capecitabine for HER2-positive advanced breast cancer. N Engl J Med 355: 2733-2743, 2006.*
Howe et al. Targeting the HER/EGFR/ERbB family to prevent breast cancer. Cancer Prev Res 4(8): 1149-1157, 2011.*
Johnston et al. Lapatanib combined with letrozole versus letrozole and placebo as first-line therapy for postmenopausal hormone receptor-positive metastic breast cancer. J Clin Oncol 27(33): 5538-5546, 2009.*
Kuerer et al. Biologic and immunologic effects of preoperative trastuzumab for ductal carcinoma in situ of the breast. Cancer 117: 39-47, published online Aug. 24, 2010.*
Kuerer et al. Ductal carcinoma in situ: state of the science and roadmap to advance the field. J Clin Oncol 27(2): 279-288, 2008.*
Olsauskas-Kuprys et al. Gamma secretase inhibitors of Notch signaling. OncoTargets Ther 6: 943-955, 2013.*
Strecker et al. Effect of lapatinib on the development of estrogen receptor-negative mammary tumors in mice. J Natl Cancer Inst 101: 107-113, 2009.*
Wang et al. Transforming growth factor beta engages TACE and ErbB3 to activate phosphatidylinositol-3 kinase/Akt in ErbB2—overexpressing breast cancer and desensitizes cells to trastuzumab. Mol Cell Biol 28(18): 5605-5620, 2008.*
Zang et al. RNAi-mediated knockdown of Notch-1 leads to cell growth inhibition and enhanced chemosensitivity in human breast cancer. Oncol Reports 23: 893-899, 2010.*
International Preliminary Report on Patentability Dated Jan. 3, 2014 From the International Bureau of WIPO Re. Application No. PCT/IL2012/050207.
Supplementary European Search Report and the European Search Opinion Dated Nov. 4, 2014 From the European Patent Office Re. Application No. 12801087.3.

(Continued)

*Primary Examiner* — Bridget E Bunner

(57) ABSTRACT

A method of treating a ductal carcinoma in situ (DCIS) lesion in a subject in need thereof is disclosed. The method comprises administering to the subject a therapeutically effective amount of a first agent capable of down-regulating activity and/or expression of at least one component participating in a NOTCH pathway, and a second agent capable of down-regulating an activity and/or expression of HER2, thereby treating the DCIS lesion.

23 Claims, 14 Drawing Sheets
(12 of 14 Drawing Sheet(s) Filed in Color)

(56) References Cited

OTHER PUBLICATIONS

Lari et al. "Biological Markers in DCIS and Risk of Breast Recurrence: A Systematic Review", Journal of Cancer, XP055149222, 2: 232-261, May 1, 2011. p. 241, 1-h Col., Lines 2-5.
Von Minckwitz et al. "Responsiveness of Adjacent Ductal Carcinoma In Situ and Changes in HER2 Status After Neoadjuvant Chemotherapy/Trastuzumab Treatment in Early Breast Cancer—Results From the GeparQuattro Study (GBG 40)", Breast Cancer Research and Treatment, XP035045645, 132(3): 863-870, Published Online Jun. 12, 2011. Abstract, p. 868, 1-h Col., Lines 2-3, r-h Col., Lines 3-6.
International Search Report and the Written Opinion Dated Aug. 2, 2012 From the International Searching Authority Re. Application No. PCT/IL2012/050207.
Farnie et al. "Ductal Carcinoma in Situ (DCIS) Mammosphere Formation; Effect of Epidermal Growth Factor (EGF) and Notch Signalling Pathways on Self Renewal Capacity", 28th Annual San Antonio Breast Cancer Symposium, San Antonio, TX, USA, Dec. 8-11, 2005, p. S14, # 25, Dec. 10, 2005.
Farnie et al. "Novel Cell Culture Technique for Primary Ductal Carcinoma In Situ: Role of Notch and Epidermal Growth Factor Receptor Signaling Pathways", Journal of the National Cancer Institute, 99(8): 616-627, Apr. 18, 2007. Abstract, Figs.1B, 3B, 3C, 5A, p. 617, r-h Col., 3rd Para, p. 621, 1-h Col., 3rd Para—p. 624, r-h Col., 3rd Para.
Han et al. "A Phase I Study of the AKT Inhibitor (MK-2206) With Concurrent Trastuzumab and Lapatinib in Patients With HER2-Positive Solid Tumors", American Society of Clinical Oncology, ASCO University Annual Meeting, Poster Discussion Session, Developmental Therapeutics—Experimental Therapeutics, Journal of Clinical Oncology, 29(Suppl.): # 3028, 201107 Jun. 2011.
Imatani et al. "Identification of a Novel NOTCH-4/INT-3 RNA Species Encoding an Activated Gene Product in Certein Human Tumor Cell Lines", Oncogene, 19: 223-231, 2000.
Korkaya et al. "HER-2, Notch, and Breast Cancer Stem Cells: Targeting an Axis of Evil", Clinical Cancer Research, 15: 1845-1847, Mar. 10, 2009.
MedlinePlus "Breast Cancer", MedlinePlus Medical Encyclopedia, 6 P., Dec. 15, 2011.
Mehta et al. "Trastuzumab Resistance: Role for Notch Signaling", The Scientific World Journal, 9: 1438-1448, Dec. 16, 2009.
Osipo et al. "ErbB-2 Inhibition Activates Notch-1 and Sensitizes Breast Cancer Cells to a Gamma-Secretase Inhibitor", Oncogene, 27(37): 5019-5032, Aug. 28, 2008. Abstract, p. 5022, r-h Col.—p. 5024, First Para, Figs.6, 7.
Pandya et al. "Targeting Both Notch and ErbB-2 Signalling Pathways Is Required for Prevention of ErbB-2-Positive Breast Tumour Recurrence", British Journal of Cancer, 105(6): 796-806, Aug. 16, 2011.
Pradeep et al. "Modeling Ductal Carcinoma in Situ: A HER2-Notch3 Collaboration Enables Luminal Filling", Oncogene, 31(7): 907-917, Jul. 11, 2011 [Online].
Reedijk ct al. "High-Level Coexpression of JAG1 and NOTCH1 Is Observed in Human Breast Cancer and Is Associated With Poor Overall Survival", Cancer Research, 65(18): 8530-8537, Sep. 15, 2005.
Stylianou et al. "Aberrant Activation of Notch Signaling in Human Breast Cancer", Cancer Research, 66(3): 1517-1525, Feb. 1, 2006.
Zardawi et al. "High Notch1 Protein Expression Is an Early Event in Breast Cancer Devlopment and Is Associated With the HER-2 Molecular Subtype", Histopathology, 56(3): 286-296, Feb. 28, 2010.

* cited by examiner

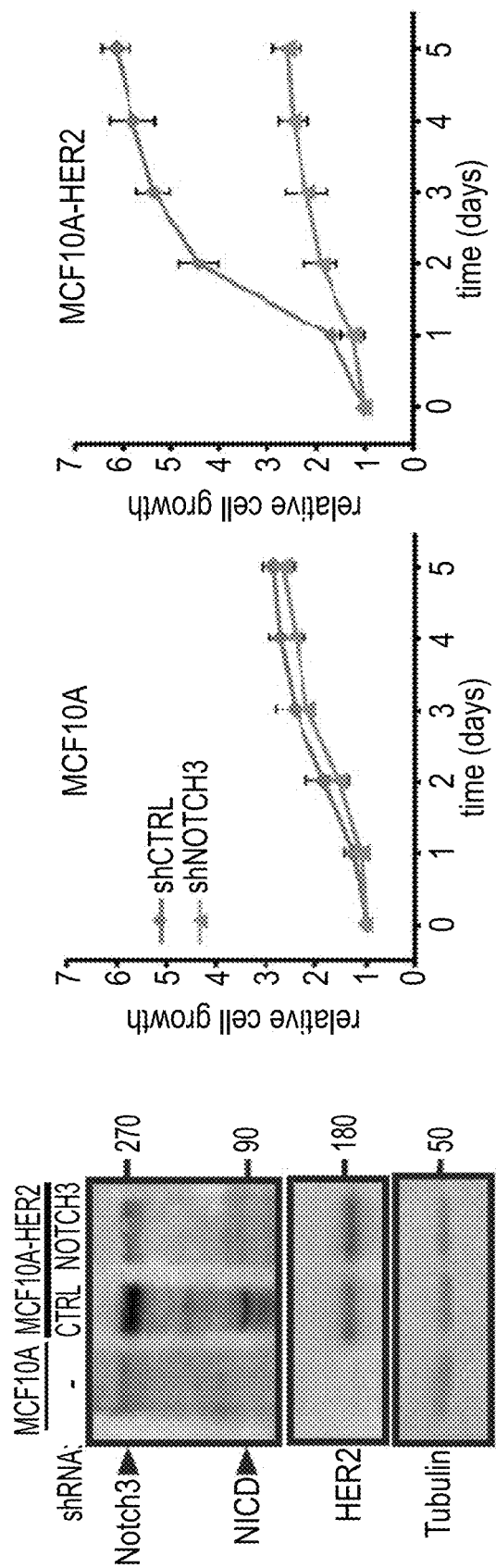

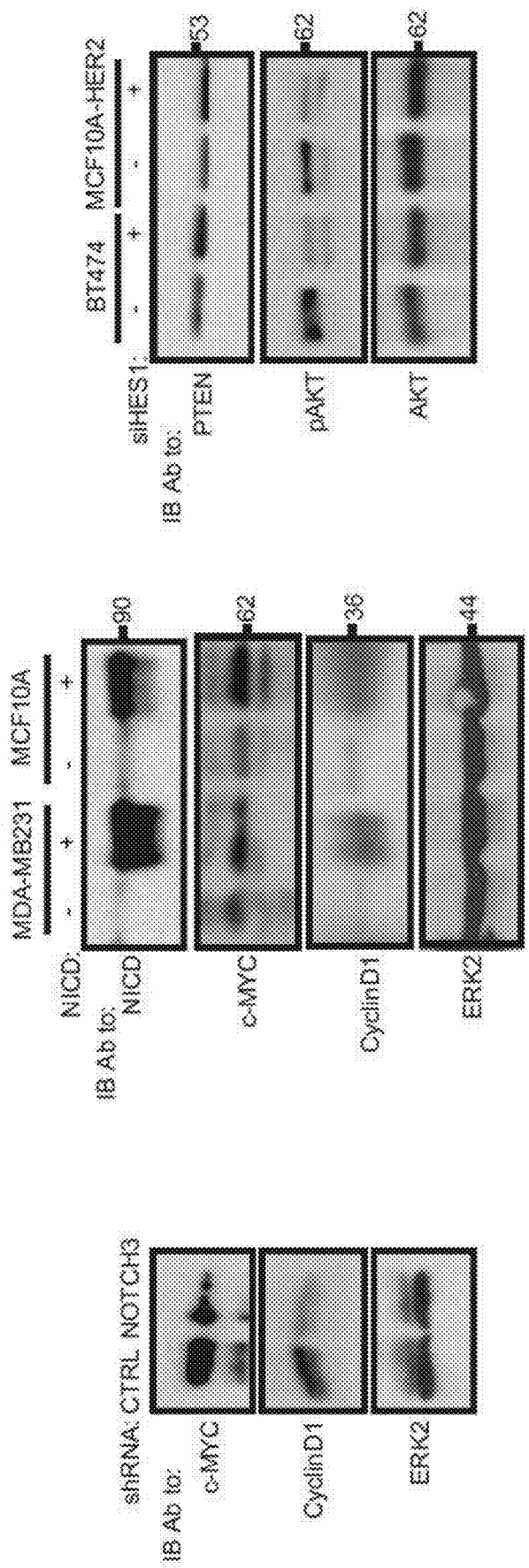

US 9,415,103 B2

SEQUENCE LISTING

```
<160> NUMBER OF SEQ ID NOS: 2

<210> SEQ ID NO 1
<211> LENGTH: 9
<212> TYPE: RNA
<213> ORGANISM: Artificial Sequence
<220> FEATURE:
<223> OTHER INFORMATION: Single strand RNA oligonucleotide

<400> SEQUENCE: 1 uucaagaga                                                              9

<210> SEQ ID NO 2
<211> LENGTH: 9
<212> TYPE: RNA
<213> ORGANISM: Artificial Sequence
<220> FEATURE:
<223> OTHER INFORMATION: Single strand RNA oligonucleotide

<400> SEQUENCE: 2 uuuguguag                                                              9
```

COMBINATION THERAPY TO PREVENT DCIS FORMATION AND PROGRESSION TO BREAST CANCER

RELATED APPLICATIONS

This application is a National Phase of PCT Patent Application No. PCT/IL2012/050207 having International filing date of Jun. 14, 2012, which claims the benefit of priority under 35 U.S.C §119(e) of U.S. Provisional Patent Application No. 61/496,577 filed on Jun. 14, 2011. The contents of the above applications are all incorporated by reference as if fully set forth herein in their entirety.

GOVERNMENT INTERESTS

Federally Sponsored Research

This invention was made with government support under CA072981 awarded by NIH. The government has certain rights in the invention.

SEQUENCE LISTING STATEMENT

The ASCII file, entitled 57986SequenceListing.txt, created on Mar. 17, 2014 comprising 759 bytes, submitted concurrently with the filing of this application is incorporated herein by reference.

FIELD AND BACKGROUND OF THE INVENTION

The present invention, in some embodiments thereof, relates to a method of treating ductal carcinoma in situ (DCIS).

The mammary gland grows rapidly at puberty to produce an elaborate tree-like structure composed of an inner layer of luminal cells, which are surrounded by an outer layer of myoepithelial cells. Later cycles of expansion and involution occur during each menstrual cycle and—even more dramatically—with each pregnancy. Mechanisms underlying formation of the lumen of mammary ducts include cell divisions with the metaphase plates organized perpendicular to the apical surface, and luminal apoptosis promoted by disengagement of inner cell layers from the basement membrane. However, the exact mechanisms that regulate duct renewal and apoptosis, as well as their relevance to malignant transformation, remain incompletely understood. In line with diverse mechanisms and cell type heterogeneity, human mammary tumors display marked morphological and molecular diversity. One aggressive subtype, comprising 20-25% of all invasive ductal carcinomas, is characterized by amplification of the HER2 gene, resulting in overexpression of the encoded HER2 oncoprotein (also known as ERBB-2/Neu). Treatment with Trastuzumab, an antibody specific to HER2, has been shown to improve outcomes for women with high-risk, early stage or metastatic breast tumors that overexpress HER2.

Another signal transduction pathway critical for breast cancer progression, comprises Notch family receptors and their membrane-bound ligands. The family includes four conserved transmembrane receptors (Notch1 through Notch4) and five surface-localized ligands (Jagged1, Jagged2, Delta-like1 through Delta-like3), which play fundamental roles in self-renewal and proliferation of progenitor and adult stem cells of the mammary gland. For instance, Notch1 and Notch3 regulate expression of c-Myc and Cyclin D1 to promote cell proliferation. Notch signaling is activated through receptor-ligand interactions between neighboring cells, resulting in successive proteolytic cleavages of Notch proteins by the tumor necrosis factor converting enzyme (TACE; also called ADAM17) and the γ-secretase complex. This releases the Notch intracellular domain (NICD) from the plasma membrane, permitting its translocation into the nucleus and formation of a trimeric transcriptional activator complex with a DNA-binding protein, CSL (also termed CBF-1 and RBP-Jκ), and Mastermind. The complex induces transcription of the HERP and HES gene families, thereby regulating the expression of multiple genes involved in cell growth, differentiation and survival.

Imatani and Callahan 2000, Oncogene 19: 223-231, Stylianou et al 2006, Cancer Res 66: 1517-1525 teach that the survival-promoting activity of the pathway likely underlays the observed ability of Notch family members to promote mammary tumors.

Reedijk et al 2005, Cancer Res 65: 8530-8537 teach that in humans, high co-expression of Notch1 and its ligand, JAG-1, associates with poor overall survival of breast cancer patients.

Osipo et al [Oncogene. 2008 Aug. 28; 27(37):5019-32, 2008] teaches administration of a HER2 inhibitor and a gamma secretase inhibitor for the treatment of breast cancer.

Han et al., [Abstract No. 3028, 2011 ASCO Annual meeting] teaches combination therapy for the treatment of cancer using a HER2 inhibitor (trastuzumab and lapatinib) and an AKT inhibitor (MK2206).

SUMMARY OF THE INVENTION

According to an aspect of some embodiments of the present invention there is provided a method of treating a ductal carcinoma in situ (DCIS) lesion in a subject in need thereof, the method comprising administering to the subject a therapeutically effective amount of a first agent capable of down-regulating activity and/or expression of at least one component participating in a NOTCH pathway, and a second agent capable of down-regulating an activity and/or expression of HER2, thereby treating the DCIS lesion.

According to an aspect of some embodiments of the present invention there is provided a method of classifying DCIS in a subject comprising analyzing an expression of HER2 and at least one component participating in a NOTCH pathway in a breast sample of the subject, wherein an expression of each of the HER2 and the at least one component participating in a NOTCH pathway above a predetermined level is indicative of an aggressive DCIS lesion.

According to still further features in the described preferred embodiments the method further comprises analyzing in a breast sample of the subject an expression of the at least one component participating in a NOTCH pathway, prior to the treating.

According to still further features in the described preferred embodiments the method further comprises analyzing in a breast sample of the subject an expression of HER2 prior to the treating.

According to still further features in the described preferred embodiments the second agent is an antibody.

According to still further features in the described preferred embodiments the antibody comprises Trastuzumab.

According to still further features in the described preferred embodiments the second agent is a kinase inhibitor.

According to still further features in the described preferred embodiments the kinase inhibitor is lapatinib.

According to still further features in the described preferred embodiments the at least one component is selected from the group consisting of Hairy and Enhancer of Split 1 (HES1), NOTCH 2 and NOTCH 3, ADAM17 and Presenilin1.

According to still further features in the described preferred embodiments the at least one component is NOTCH3.

According to still further features in the described preferred embodiments the first agent is an siRNA molecule.

According to still further features in the described preferred embodiments the first agent is a gamma secretase inhibitor, a mitogen-activated protein kinase kinase (MEK) specific inhibitor or a PI3K-AKT inhibitor.

According to still further features in the described preferred embodiments the first agent is a gamma secretase inhibitor.

According to still further features in the described preferred embodiments the component participating in a NOTCH pathway is selected from the group consisting of NOTCH3, HES1 and presenilin.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
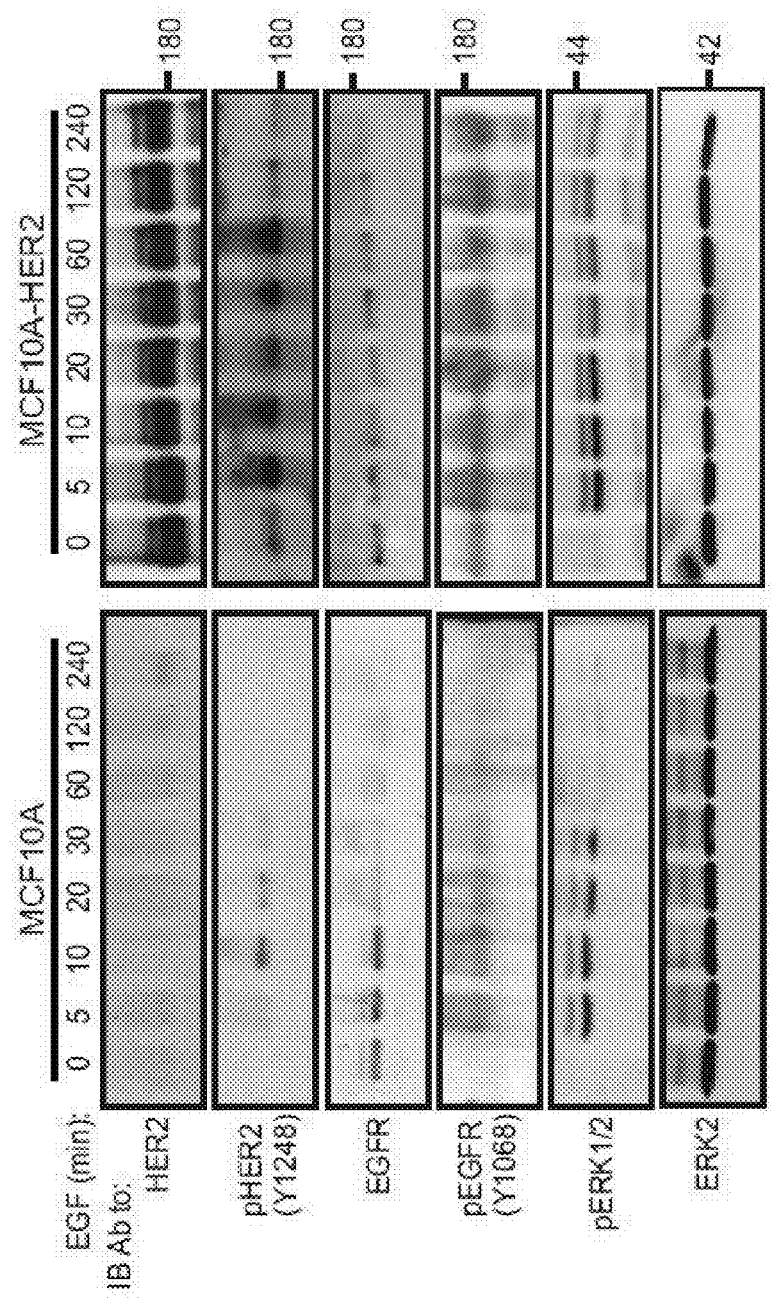
Figure 1B:
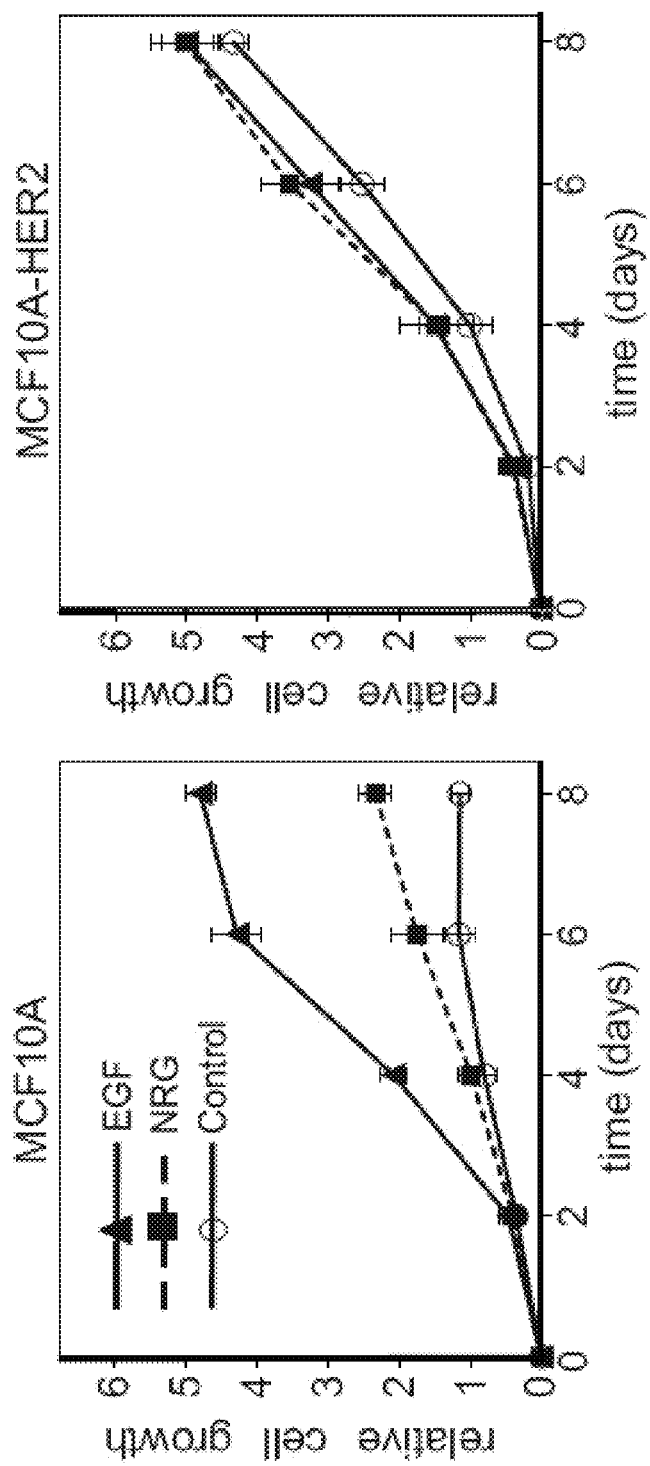

FIGS. 1A-B illustrate that ectopic overexpression of HER2 releases monolayers of mammary cells from growth saturation and from reliance on growth factors. (1A) Monolayers of MCF10A cells stably expressing the plasmid IRES-GFP (MCF10A) or HER2-IRES-EGFP (MCF10A-HER2) were starved for 24 hours and stimulated with EGF (20 ng/ml) for the indicated time intervals. Cell lysates were electrophoresed and immunoblotted (IB) with the indicated antibodies. (1B) MCF10A and MCF10A-HER2 cells were grown for up to 8 days in the presence or absence of EGF or NRG-1β (each at 20 ng/ml). Cell growth was monitored using the MTT assay. Data represent averages ±S.D. of triplicates. The experiment was repeated thrice.

FIGS. 2A-F illustrate that HER2 transcriptionally induces multiple components of the Notch pathway. (2A) Expression heatmaps of Notch pathway genes, whose expression levels, as determined using oligonucleotide microarrays, differ between spheroids of MCF10A and MCF10A-HER2 cells seeded in Matrigel™ (day 0) and cultured for the indicated time intervals. The color bar depicts relative expression levels. (2B) Quantitative real-time PCR (qRT-PCR) was used for validation of microarray expression profiles of selected Notch pathways genes in MCF10A and MCF10A-HER2 spheroids seeded at day 0 and cultured in Matrigel™ for the indicated time intervals. (2C) qRT-PCR analyses of selected Notch pathway genes in MCF10A-HER2 spheroids incubated for up to five days in the absence or presence of the MEK inhibitor U0126 (1 μM). (2D) Confocal photomicrographs showing GFP-expressing MCF10A and MCF10A-HER2 spheroids immunostained for Laminin V (left panels), or for Notch3 (right panels), eight days after seeding single cells in Matrigel™. Scale bars, 50 μm. (2E) Monolayers of MCF10A and MCF10A-HER2 cells were starved for 12 hours and stimulated with EGF (20 ng/ml) for the indicated time intervals. Cell lysates were immunoblotted with the indicated antibodies. NICD, Notch intracellular domain. (2F) Monolayers of MCF10A and MCF10A-HER2 cells were grown in serum-free medium, immunostained for Notch3 (red) and nuclei counterstained with DAPI (blue). The inset (broken line rectangle; magnified in the right panel) shows nuclear localization of Notch3, likely representing the cleaved intracellular domain. Scale bar, 20 μm.

FIGS. 3A-D illustrate that enhanced survival and proliferation of HER2-overexpressing cells are enabled by Notch3. (3A) Extracts of monolayers of MCF10A cells and MCF10A-HER2 cells stably expressing control shRNA or shRNA targeting Notch3 were immunoblotted with the indicated antibodies. (3B) Proliferation of monolayer MCF10A and MCF10A-HER2 cells stably expressing the indicated shRNAs was determined using the MTT assay. Averages and standard deviation values (bars) of triplicates are presented. (3C) MCF10A and MCF10A-HER2 cells stably expressing the indicated shRNAs were cultured for 8 days in poly-HEMA-coated wells and photographed using a phase contrast microscope (upper part; scale bar, 100 μm). The number of spheroids per well was determined in triplicates and the average and standard deviations (bars) are presented (lower left panel). For MCF10A-HER2 cells, we estimated the volume of 120 spheroids per condition and presented the average volume and the standard errors (bars). (3D) MCF10A cells and MCF10-HER2 cells stably expressing control shRNAs or shRNAs targeting Notch3 were grown in Matrigel™ for the indicated time intervals and images captured by confocal microscopy. The upper row shows immunostaining for cleaved (active) Caspase-3 (scale bar, 25 μm), whereas the lower panels present the anatomy of the GFP-expressing spheroids (scale bar, 50 μm). The bar graph presents the average fractions (±S.D., bars) of lumen-filled spheroids, as determined by analyzing 100 spheroids of each group.

FIGS. 4A-G illustrate that Notch3 promotes survival of HER2-overexpressing mammary cells. (4A) The relative expression levels of transcripts corresponding to c-Myc and Cyclin D1 (CCND1) were determined by applying quantitative real-time PCR to RNA samples from MCF10A and MCF10A-HER2 spheroids. (4B) MCF10A and MCF10A-HER2 cells were grown in Matrigel™ for 4 days and then the resulting spheroids were incubated in the presence of Trastuzumab (10 μg/ml) and/or a gamma-secretase inhibitor (GSI, 1 μM). Two days later, cells were extracted and subjected to immunoblotting, as indicated. (4C) Monolayers of MCF10A-HER2 cells stably transduced with control or Notch3 shRNAs were lysed and immunoblotted for c-Myc and Cyclin D1. (4D) Monolayers of MDA-MB231 and MCF10A cells were transfected with pCDNA3.1-Notch3-NICD or with an empty plasmid, lysed 48 hours later and immunoblotted using the indicated antibodies. (4E) BT474 and MCF10A-HER2 cells were grown in monolayers and transfected with control or HES1-specific siRNA oligonucleotides, followed by lysis 48 hours later and immunoblotting with the indicated antibodies.

(4F) MCF10-HER2 spheroids were grown in Matrigel™ for 4 days and then incubated with Trastuzumab and/or GSI for up to 4 additional days. Confocal microphotographs show acinar morphology of GFP-expressing cells, along with staining for the cleaved form of Caspase-3 in the upper panels. Scale bars, 50 µm. The fraction of lumen-filled spheroids on day 8 was quantified by counting 100 spheroids in each treatment group. Data denote averages (±S.D.) of triplicates. (4G) MCF10-HER2 cells were grown in Matrigel™ for 4 days, and then incubated for up to 4 additional days in the presence of inhibitors of c-Myc (10058-F4; 1 µM), PI3K (LY-294002; 2 µM) or MEK (U0126; 1 µM). The upper panels show confocal images of spheroids captured on day 6 after immunostaining for cleaved Caspase-3 (red) and counterstaining with DAPI (blue). The lower panels show structures formed by GFP-expressing cells on day 8. Scale bars, 50 µm. The fractions of filled spheroids were determined as in FIG. 4F.

Figure 5A:
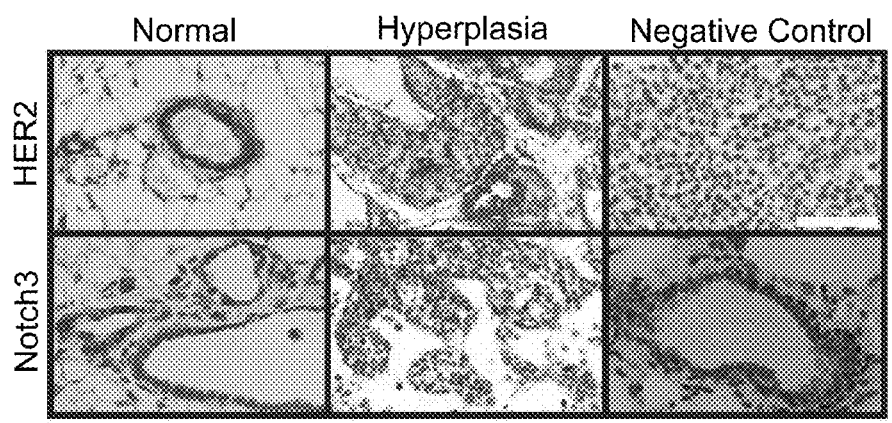
Figure 5B:
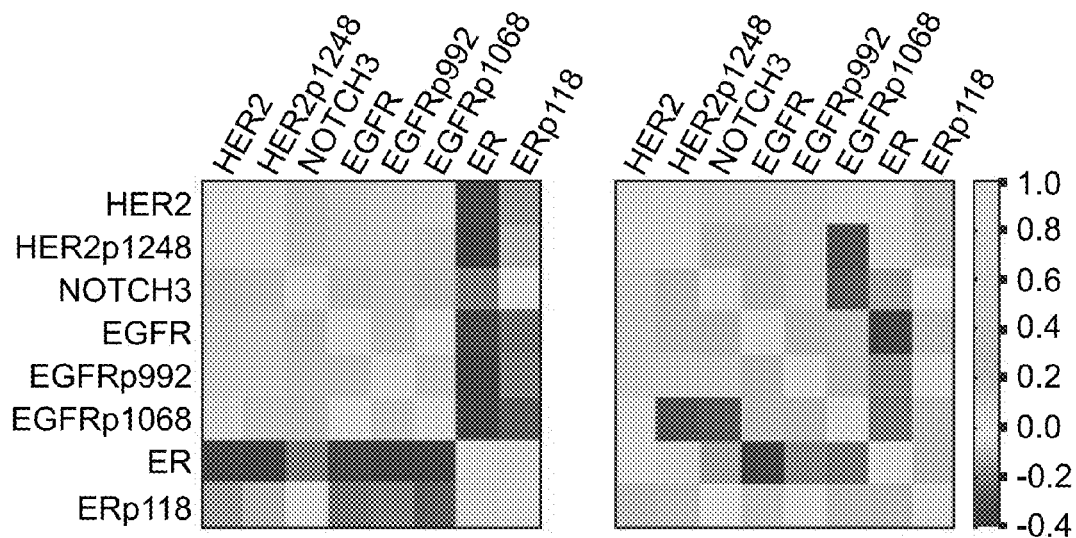
Figure 5C:
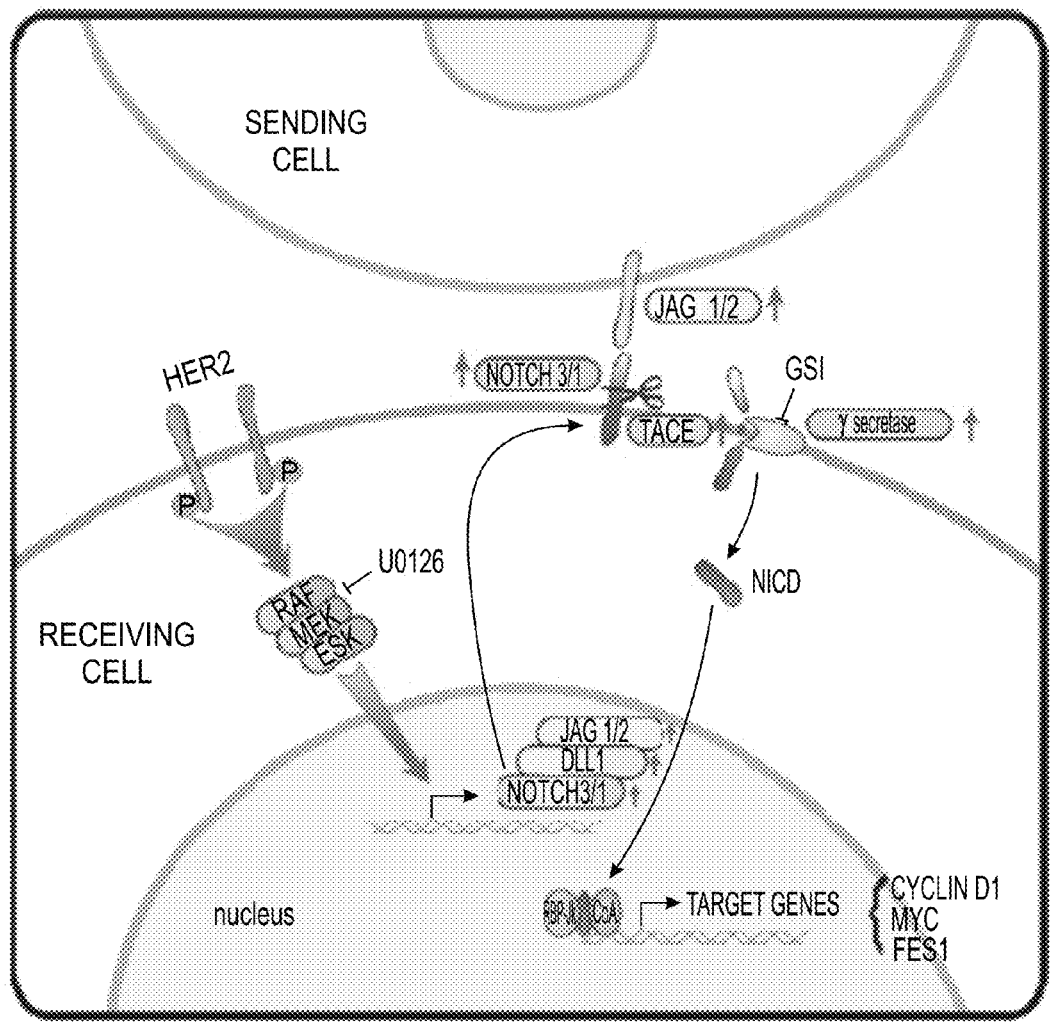

FIGS. 5A-C illustrate that Notch3 expression correlates with HER2 levels in human mammary tumors and in an animal model overexpressing HER2. (5A) Immunohistochemical analyses of HER2 and Notch3 expression in mammary glands of normal mice, as well as in regions of hyperplasia of MMTV-HER2 mice. Scale bar, 200 µm. (5B) Lysates of invasive breast cancer specimens were analyzed using reverse phase protein arrays (RPPA) for expression of Notch3, along with the levels of total and phosphorylated forms of EGFR, HER2 and ER. Two independent patient cohorts were employed: Cohort 1: left heatmap, n=102 patients; (Speers et al, 2009), and Cohort 2: right heatmap, n=95 patients. Heatmaps show correlation matrices of protein expression and the color scheme corresponds to Pearson correlation coefficients (r). Note high correlation between Notch3 and the phosphorylated form of HER2 (p1248) in both cohorts (r=0.43, p=1.55E-05 for the left cohort, and r=0.23, p=2.58E-02 for the right cohort). (5C) Schematic presentation of the effects of HER2 on the Notch pathway, specifically referring to components up-regulated (red vertical arrows) in HER2-overexpressing MCF10A cells. NICD, Notch intracellular domain.

DESCRIPTION OF SPECIFIC EMBODIMENTS OF THE INVENTION

The present invention, in some embodiments thereof, relates to a method of treating ductal carcinoma in situ (DCIS).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

A large fraction of ductal carcinoma in situ (DCIS), a non-invasive precursor lesion of invasive breast cancer, over-expresses the HER2/neu oncogene. The ducts of DCIS are abnormally filled with cells that evade apoptosis. In order to understand the underlying mechanisms behind this phenomenon, the present inventors over-expressed HER2 in mammary epithelial cells and observed growth factor-independent proliferation. When grown in extracellular matrix as 3-dimensional spheroids, control cells developed a hollow lumen, but HER2-overexpressing cells populated the lumen by evading apoptosis. HER2 overexpression in this cellular model of DCIS was shown to drive transcriptional up-regulation of multiple components of the Notch survival pathway. Importantly, luminal filling required up-regulation of a signaling pathway comprising Notch3, its cleaved intracellular domain (NICD) and the transcriptional regulator HES1, resulting in elevated levels of c-Myc and Cyclin D1. In line with HER2-Notch3 collaboration, drugs intercepting either arm reverted the DCIS-like phenotype. Thus, the present inventors propose combination therapy targeting both HER2 and Notch to delay the putative transition from DCIS to infiltrating ductal carcinoma overexpressing the HER2 oncoprotein.

Furthermore, the present inventors found an association between HER2 levels and expression levels of components of the Notch pathway in tumor specimens of breast cancer patients. Therefore, the present inventors propose that analysis of expression of HER2 and components of the NOTCH pathway in a breast cell sample may serve as an aid for diagnosis and/or classification of such cancers.

Thus, according to one aspect of the present invention there is provided a method of treating a ductal carcinoma in situ (DCIS) lesion in a subject in need thereof, the method comprising administering to the subject a therapeutically effective amount of a first agent capable of down-regulating activity and/or expression of at least one component participating in a NOTCH pathway and a second agent capable of down-regulating an activity and/or expression of HER2, thereby treating the DCIS lesion.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "DCIS lesion" denotes a breast lesion that is contained within the milk ducts of the breast. DCIS lesions contain some cells with malignant features but not all such lesions behave as cancer, for example, they will not spread outside the ducts and invade surrounding breast tissue, nor will they be life threatening. DCIS has been described as a non-obligate precursor of breast cancer and as non-invasive cancer.

As used herein, the term "subject" refers to a mammalian subject, preferably a human.

The phrase "component participating in the NOTCH pathway" refers to a polypeptide or polynucleotide involved in the NOTCH signaling pathway. Exemplary components are described herein below.

The Notch signaling pathway is a conserved intercellular signaling mechanism.

Members of the Notch gene family (NOTCHs) encode transmembrane receptors that are critical for various cell fate decisions. Multiple ligands that activate Notch and related receptors have been identified, including Serrate and Delta in *Drosophila* and JAG1 (MIM.601920) in vertebrates.

Four different Notch receptors (NOTCHs: NOTCH1 to NOTCH4) and five ligands (Jagged-1 (JAG1) and -2 (JAG2) and Delta-like [DLLs]: DLL1, DLL2 and DLL4) have been characterized in mammalian cells. These transmembrane receptors and ligands are expressed in different combinations in most, if not all, cell types. The Notch pathway regulates cell fate determination of neighbouring cells through lateral inhibition, depending on their ability to express either the receptors or the ligands.

Following ligand binding, NOTCHs are activated by a series of cleavages that releases its intracellular domain (NICD). This processing requires the activity of two proteases, namely ADAM17 (tumour necrosis factor-α converting enzyme or TACE MIM.603369) and presenilin-1 (PSEN1 MIM.104311), both of which also fall under the category of a component of a NOTCH pathway.

Nuclear translocation of NICD results in transcriptional activation of genes of the HESs family (Hes/E(sp1) family) and HEYs family (Hesr/Hey family) through interaction of NICD with RBPSUH (or CBF1 MIM.147183), Su(H), and Lag-1, which is also known as the recombination signal sequence-binding protein (RBP)-j (also called Suppressor of Hairless, Su(H)), each of these also falling under the category of a component of a NOTCH pathway.

Overall, when activated, Notch signalling enables neighbouring cells to acquire distinct phenotypes, through a process named lateral inhibition. The Notch receptor is pre-cleaved in the Golgi and is targeted subsequently to the plasma membrane where it interacts with ligands located on neighbouring cells. Receptor-ligand interaction results in a conformational change in the receptor, thus enabling additional cleavages by TACE and the γ-secretase complex. This proteolytic activity enables the Notch intracellular domain (NICD) to translocate to the nucleus where it activates the transcription of target genes (e.g. the HES and HERP family of transcriptional repressors).

Monoubiquitylation (Ub) of the ligand by mindbomb (MIB) induces endocytosis of the ligand and the Notch extracellular domain (NECD) into the ligand cells where additional signalling might be initiated.

Notch receptors undergo a complex set of proteolytic processing events in response to ligand activating, which eventually leads to release of the intracellular domain of the receptor. Signal transduction is normally initiated by binding to transmembrane ligands of the Serrate or Delta class, which induces proteolytic release of the intracellular NOTCH domain (NICD).

Free NICD translocates to the nucleus to form a short-lived complex with a Rel-like transcription factor, CSL, and Mastermind-like co-activators that activates lineage-specific programs of gene expression.

As mentioned, the present invention contemplates down-regulating any component of the NOTCH pathway that is up-regulated in DCIS above a predetermined threshold.

Methods of analyzing whether a particular component is upregulated in DCIS are known in the art, and may be effected on the RNA level (using techniques such as Northern blot analysis, RT-PCR and oligonucleotides microarray) and/or the protein level (using techniques such as ELISA, Western blot analysis, immunohistochemistry and the like, which may be effected using antibodies specific to the NOTCH pathway component).

According to one embodiment the NOTCH pathway component (and HER2) is upregulated by at least 1.5 times, more preferably by at least 2 times and more preferably by at least 3 times in the DCIS as compared to normal, control breast tissue.

According to another embodiment, the NOTCH pathway component is Hairy and Enhancer of Split 1 (HES1; NM_005524, NP_005515), NOTCH1 (NM_017617, NP_060087.3) NOTCH 2 (NM_024408, NP_077719.2) and NOTCH 3 (NM_000435, NP_000426.2).

According to another embodiment, the NOTCH pathway component is Hairy and Enhancer of Split 1 (HES1; NM_005524, NP_005515), NOTCH 2 (NM_024408, NP_077719.2) or NOTCH 3 (NM_000435, NP_000426.2).

According to another embodiment, the NOTCH pathway component is Hairy and Enhancer of Split 1 (HES1), NOTCH 2 and NOTCH 3, ADAM17 or Presenilin1.

As mentioned, the method of this aspect of the present invention involves a combination of down-regulating an NOTCH pathway component as well as down-regulating an activity and/or expression of HER2.

As used herein "HER2" refers to a receptor tyrosine kinase (RTK) of the epidermal growth factor receptor family, E.C. 2.7.10.1 also referred to as ErbB-2, NEU and p185erbB-2.

Downregulation of NOTCH pathway components and HER2 can be effected on the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

According to one embodiment the agents used to down-regulate NOTCH pathway components and/or HER2 are antibodies.

Antibodies of this aspect of the present invention can be selected from pre-existing antibodies (e.g., publicly available hybridomas or recombinant antibody libraries, further described hereinbelow) or from newly generated antibodies produced according to methods which are well-known in the art and are further described hereinbelow.

Antibodies and methods of generating same are described at length in the following sections.

The term "antibody" as used in this invention includes intact molecules as well as functional fragments thereof, such as Fab, F(ab')2, and Fv. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

Methods of identifying the binding epitopes of antibodies are well known in the art. Briefly, antibody binding epitopes can be determined by an antibody displacement assay. This may provide an initial understanding to the binding site. Antibody displacement techniques are well known in the art. At times a finer analysis is required, to this end epitope mapping techniques are employed. In this case the method of peptide scanning by Reineke et al. 1999 is typically employed (Curr. Top. Microbiol. Immunol. 243:23-36).

According to one embodiment, the antibody which recognizes HER2 binds the HER2 dimerization site (i.e., binding of the antibody thereto is sufficient for blocking HER2 dimerization). Examples of such antibodies are provided in WO2010/029534, incorporated herein by reference.

According to another embodiment, the antibody which recognizes HER2 is Herceptin®/Trastuzumab.

Preferably, the antibodies contemplated by the present invention bind to their respective targets with a minimal affinity of at least 1 µM, 200 nM, 100 nM, 1 nM or higher.

Downregulation of HER2 and/or a component of the NOTCH pathway can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., HER2 and/or a component of the NOTCH pathway) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplates use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573: 127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (SEQ ID NO: 1; Brummelkamp, T. R. et al. (2002) Science 296: 550) and 5'-UUUGUGUAG-3' (SEQ ID NO: 2; Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to a specific embodiment the agent is an siRNA directed against HES1.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with some embodiments of the invention can be effected as follows. First, the selected mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.dotambion:dotcom/techlib/tn/91/912dothtml, Ambion website).

Second, potential target sites are compared to an appropriate genomic database (e.g., human, mouse, rat etc.) using any sequence alignment software, such as the BLAST software available from the NCBI server (worldwidewebdotncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, plsl, TAT(48-60), pVEC, MTS, and MAP.

Another agent capable of downregulating HER2 and/or a member of the NOTCH pathway is a DNAzyme molecule capable of specifically cleaving an mRNA transcript or DNA sequence of the HER2 and/or a member of the NOTCH pathway. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of HER2 and/or a member of the NOTCH pathway can also be effected by using an antisense polynucleotide capable of specifically hybridizing with an mRNA transcript encoding HER2 and/or the member of the NOTCH pathway.

Another agent capable of downregulating HER2 and/or a member of the NOTCH pathway is a ribozyme molecule capable of specifically cleaving an mRNA transcript encoding HER2 and/or the member of the NOTCH pathway.

Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications.

An additional method of regulating the expression of HER2 and/or the member of the NOTCH pathway in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251: 1360-1363; Cooney, M., et al., Science, 1988; 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo  | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub).

The same authors have demonstrated that TFOs designed according to the A-AT and G-GC rule do not form non-specific triplexes, indicating that the triplex formation is indeed sequence specific.

Thus for any given sequence in the HER2 and or component of the NOTCH pathway regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Another agent capable of downregulating a NOTCH pathway component and/or HER2 would be any molecule which binds to and/or cleaves the NOTCH pathway component and/or HER2. Such molecules can be NOTCH pathway component and/or HER2 antagonists, or NOTCH pathway component and/or HER2 inhibitory peptide.

It will be appreciated that a non-functional analogue of at least a catalytic or binding portion of NOTCH pathway component and/or HER2 can be also used as the active agent.

Another agent which can be used along with some embodiments of the invention to downregulate NOTCH pathway component and/or HER2 is a molecule which prevents its activation or DNA binding.

Additional agents for contemplating a member of the NOTCH pathway include a gamma secretase inhibitor, a MEK specific inhibitor or a PI3K-AKT inhibitor.

Examples of gamma secretase inhibitors include, but are not limited to semagacestat ((2S)-2-Hydroxy-3-methyl-N-[(1S)-1-methyl-2-oxo-2-[[(1S)-2,3,4,5-tetrahyd-ro-3-me-thyl-2-oxo-1H-3-benzazepin-1-yl]amino]ethyl]butanamide, also known as LY450139; Eli Lilly and Co.), Compound E (R2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], available from Alexis Biochemicals), LY411575 (Eli Lilly and Co.), L-685,458 (Sigma-Aldrich), BMS-289948 (4-chloro-N-(2,5-difluorophenyl)-N-41R)-14-fluoro-2-[3-(1H-imidazol-1-yl-) propyl]phenyl}ethyl)benzenesulfonamide hydrochloride) and BMS-299897 (4-[2-((1R)-1-1 [(4-chlorophenyl)sulfonyl]-2,5-difluoroanilino}ethyl)-5-fl-uorophenyl]butanoic acid) (Bristol Myers Squibb), MK0752 (Merck), and MRK-003 (Merck). These and other agents are described in Rizzo et al., Oncogene 27:5124-5131 (2008); Olson and Albright, Current Topics Medicinal Medicine 8:17-33 (2008); Graziani et al., Cancer Res. 68:9678-9685 (2008); Rao et al., Cancer Res. 69:3060-3068 (2009); Sharma et al., Mol. Cell. Biol. 26:8022-8031 (2006); Cullion et al., Blood. 113:6172-6181 (2009); Cho et al., J. Immunol. 182:3380-3389 (2009); Samon et al., Blood 112:1813-1821 (2009); Joshi et al., Blood 113:1689-1698 (2009); Fleisher et al., Arch. Neurol. 65:1031-1038 (2009); Lanz et al., J. Pharmacol. Exp. Therapeutics 319:924-933 (2006); Spilman et al., PNAS 105: 10595-10600 (2008); and Namihira et al., Dev Cell 16:245-255 (2009).

A MEK inhibitor refers to any inhibitor of a member of the MEK family of protein kinases, including MEK1, MEK2 and MEK5. Examples of suitable MEK inhibitors, already known in the art, include the MEK1 inhibitors PD184352 and PD98059, inhibitors of MEK1 and MEK2 U0126 and SL327, and those discussed in Davies et al. Biochem J., 351:95-105, 2000.

Other MEK inhibitors and classes of MEK inhibitors are described in Zhang et al. Bioorganic Med. Chem. Letters; 10:2825-2828 (2000). Inhibitors of MEK can include antibodies to, dominant negative variants of, and siRNA and antisense nucleic acids that suppress expression of MEK. Specific examples of MEK inhibitors include, but are not limited to, PD0325901, PD98059 (available, e.g., from Cell Signaling Technology), U0126 (available, for example, from Cell Signaling Technology), SL327 (available, e.g., from Sigma-Aldrich), ARRY-162 (available, e.g., from Array Biopharma), PD184161, PD184352 (CI-1040), sunitinib (see, e.g., Voss, et al., US2008004287) incorporated herein by reference), sorafenib (see, Voss supra), Vandetanib (see, Voss supra), pazopanib (see, e.g., Voss supra), Axitinib (see, Voss supra) and PTK787 (see, Voss supra).

Currently, several MEK inhibitors are undergoing clinical trial evaluations. CI-1040 has been evaluated in Phase I and II clinical trials for cancer. Other MEK inhibitors being evaluated in clinical trials include PD 184352 (see, e.g., English et al., 2002), BAY 43-9006 (see, e.g., Chow et al., 2001), PD-325901 (also PD0325901), GSK1 120212, ARRY-438162, RDEA1 19, AZD6244 (also ARRY-142886 or ARRY-886), R05126766, XL518 and AZD8330 (also ARRY-704).

Phosphoinositide 3-kinase (PI3K)-protein kinase B (AKT) inhibitor refers to an agent which down-regulates a component of a signaling pathway that includes the phosphorylation of an Akt protein by a PI3K protein.

Examples of such inhibitors include, but are not limited to wortmannin and LY294002.

An example of an HER2 inhibitor contemplated by the present invention include Lapatinib. It binds to the intracellular phosphorylation domain of HER2 to prevent receptor autophosphorylation upon ligand binding. Other HER2 inhibitors include, but are not limited to gefitinib, erlotinib, cetuximab, ABX-EGF, HKI272, AEE-788, BIBW-2992, TAK165, BMS-599626, canertinib, EKB-569 or PKI-166.

The agents described herein may be provided per se or as part of a pharmaceutical composition where they are mixed with suitable carriers or excipients (either individually or in a co-formulation).

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

As used herein, the term "active ingredient" refers to the active agents described herein accountable for the intended biological effect.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose.

By "therapeutically effective amount or dose" or "therapeutically sufficient amount or dose" or "effective or sufficient amount or dose" herein is meant a dose that produces therapeutic effects for which it is administered, in the context of the combination therapy in which it is administered. Often, the therapeutically effective or sufficient amount or dose of the compounds comprising the pharmaceutical compositions of the invention will be lower when administered in the specific combinations, than the doses that would be therapeutically effective or sufficient when the compounds are administered separately. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington. The Science and Practice of Pharmacy, 20th Edition, 2003, Gennaro, Ed., Lippincott, Williams & Wilkins). In some embodiments, a therapeutically effective amount refers to that amount of the therapeutic agent sufficient to reduce the amount of DCIS. A therapeutically effective amount may refer to the amount of therapeutic agent sufficient to delay or minimize the spread of cancer. A therapeutically effective amount may also refer to the amount of the therapeutic agent that provides a therapeutic benefit in the treatment or management of cancer. Further, a therapeutically effective amount with respect to a therapeutic agent of the invention means that amount of therapeutic agent alone, or in combination with other therapies, that provides a therapeutic benefit in the treatment or management of cancer. In sensitized cells, the therapeutically effective dose can often be lower than the conventional therapeutically effective dose for non-sensitized cells. In some embodiments, a therapeutically effective amount refers to the amount of a therapeutic agent that, e.g., reduces the proliferation of cancer cells, increases the death of cancer cells or, reduces the size of a tumor or spread of a tumor in a subject. Preferably, a therapeutically effective amount of a therapeutic agent reduces the amount of a DCIS or the spread of a tumor in a subject by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as PBS. In some embodiments, a therapeutically effective amount refers to the amount of a therapeutic agent that increases survival by 1 month, 2 months, 6 months, 1 year, 2 years, 3 years, 4 years, 5 years, 6 years, 7 years, 8 years, 9 years, 10 years, or more. In some embodiments, a therapeutically effective amount refers to the amount of a therapeutic agent that prevents the progression from DCIS or atypical hyperplasia to breast cancer.

In certain embodiments, the HER2 antibody (e.g. trastuzumab-MCC-DM1) is combined in a pharmaceutical combination formulation, or dosing regimen as combination therapy, with a second compound that is capable of down-regulating a NOTCH pathway component. NOTCH pathway inhibitor of the pharmaceutical combination formulation or dosing regimen preferably has complementary activities to the HER2 antibody, and such that they do not adversely affect each other.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the HER2 inhibitor and the NOTCH pathway inhibitor.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.).

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

It is expected that during the life of a patent maturing from this application many relevant NOTCH pathway and HER2 inhibitors will be developed and the scope of the term NOTCH pathway and HER2 inhibitor is intended to include all such new technologies a priori.

Another clinical implication of the finding described herein is for classifying DCIS patients.

The determination of the aggressiveness phenotype of the DCIS lesion may be used to develop a treatment plan for the subject with the DCIS lesion. As noted above, most DCIS is indolent, but due to the propensity of some DCIS to become invasive many subjects with DCIS are treated aggressively. A reliable test to determine the propensity of a DCIS lesion to progress to invasive cancer would save many patients from undergoing needless procedures and would reduce health care costs. Those subjects whose lesions are likely indolent may be treated by monitoring the lesion over time. Those subjects whose lesions are likely aggressive can receive aggressive therapy, such as surgery, radiation, chemotherapy or a combination thereof. Furthermore, co-incidence of HER2 and active Notch may identify a group of DCIS patients who are at increased risk of relapse after surgery. Thus, the results of the methods provided herein may be used to develop treatment plans for the subject or may be used as a prognostic assay to provide physicians with additional information.

Thus, according to another aspect of the present invention there is provided a method of classifying DCIS in a subject comprising analyzing an expression of HER2 and at least one component participating in a NOTCH pathway in a breast sample of the subject, wherein an expression of each of the HER2 and the at least one component participating in a NOTCH pathway above a predetermined level is indicative of an aggressive DCIS lesion.

Typically, when the expression of the at least one component of the NOTCH pathway is upregulated by more than 2 fold, more than 3 fold, more than 5 fold, the DCIS is classified as high grade and more aggressive therapy (e.g. surgery) is suggested.

Methods of analyzing expression of a component of the NOTCH pathway and HER2 are described herein above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed.

(1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Reagents, cell lines, animals and breast tumor samples: Unless indicated, reagents were purchased from Sigma (St. Louis, Mo.) and antibodies from Santa Cruz Biotechnology. The Notch3 antibody was purchased from Cell Signaling Technology (Beverly, Mass.). HRP-conjugated antibodies were from the Jackson Laboratories (Bar Harbor, Me.). HES1 siRNA was from Dharmacon (Lafayette, Colo., USA). The following buffers were used: TBST: 20 mM Tris-HCl (pH 7.5), 0.15 M NaCl, and 0.05% Tween20. Solubilization buffer: 50 mM HEPES (pH 7.5), 150 mM NaCl, 10% glycerol, 1% Triton X-100, 1 mM EDTA, 1 mM EGTA, 0.2 mM $Na_3VO_4$ and a protease inhibitor cocktail. Cell growth was assayed by using a 3-(4,5-dimethylthiazol-z-yl)-2,5-diphenyl tetrazolium bromide (MTT) based kit. BT-474 cells were maintained in DME/F12 with 10% serum and antibiotics, and MCF10A cells were maintained as previously described (Katz et al 2007). Mammary fat pads of HER-2/neu transgenic or wild type FVB mice (Jackson Laboratories) were processed as previously described (Tekmal et al 2007). Breast tumor samples for RPPA were obtained from the Baylor College of Medicine Breast Centre Anonymized Tumor Bank (Cohort 1; (Speers et al, 2009)) and the M.D. Anderson Cancer Centre Tumor Bank (Cohort 2).

Retroviral infection: pBMN-HER2-IRES-EGFP or pBMN-IRES-EGFP (control) were co-transfected with a retroviral packaging plasmid, pSV-ψ-env-MLV into 293T cells using FuGENE (Roche Applied Science, Indianapolis). Virus-containing medium was collected 48-72 hours later and passed through a 45-μm filter. MCF10A cells were transduced with control or HER2-encoding retroviral vectors and cells stably expressing GFP after 5 passages were selected by flow cytometry.

Morphogenesis assays: Cells were gently trypsinized, washed and re-suspended in assay medium (DME/F12 supplemented with 2% horse serum, 10 μg/ml insulin, 1 ng/ml cholera toxin, 100 μg/ml hydrocortisone, and antibiotics) to a concentration of $10^5$ cells per 4.0 ml. Eight-well chambered slides (BD Biosciences) were coated with 35 μl Matrigel™ per well and left to solidify for 15 minutes. Cells were mixed 1:1 with assay medium containing 5% Matrigel™, 20 ng/ml EGF, and 0.4 ml added to each chamber. Each morphometric quantification was performed in triplicates and repeated thrice.

Immunofluorescence and confocal microscopy: Acinar structures were fixed on glass slides for 10 minutes in methanol-acetone (1:1; −20° C.), and air-dried before blocking for 1 hour at room temperature in immunofluorescence buffer (130 mM NaCl, 7 mM $Na_2HPO_4$, 3.5 mM $NaH_2PO_4$, 7.7 mM $NaN_3$, 0.1% bovine serum albumin, 0.2% Triton X-100 and 0.05% Tween-20 and 10% goat serum). Secondary blocking was performed for 30 minutes in immunofluorescence buffer containing goat anti-mouse F(ab')$_2$ fragment (20 μg/ml). The primary antibody was incubated at 4° C. for 15-18 hours. Secondary antibodies conjugated to fluorescent dyes and diluted in blocking buffer were subsequently incubated for 60 minutes at room temperature. Immunofluorescent images were acquired using an inverted microscope equipped with a digital camera and SPOT software. Confocal microscopy was performed using Bio-Rad Radiance 2000 platform equipped with a Nikon eclipse TE300 microscope (Oberkochen, Germany). Images presented are representative of three or more independent experiments.

Real-Time quantitative PCR and oligonucleotide microarray hybridization: Total RNA was isolated using a Versagene kit (Gentra Systems, Minneapolis) and reverse transcribed with random hexamers (SuperScript II first-strand synthesis kit, InVitrogen, California). Real-time PCR analysis was performed using SYBR Green I (Applied Biosystems) in triplicates, and the results were normalized to beta-2 microglobulin. For oligonucleotide microarray hybridization, RNA (10 μg) was labeled, fragmented and hybridized to Affymetrix HuGENE 1.0 ST arrays. After scanning of the arrays, gene expression values were calculated and the results were normalized using the expression console of Affymetrix (RMA normalization).

Mammosphere cultures in polyHEMA: Mammospheres were cultured in polyHEMA as previously described (Dontu et al 2003). Briefly, 2,000 cells were plated into each well of polyHEMA-coated 24-well plates (Corning, Massachusetts) and grown in serum-free mammary epithelial growth medium (Biowhittaker, Rockland, Me.) supplemented with B27 (Invitrogen, Carlsbad, Calif.).

Reverse-Phase protein arrays (RPPA): Preparation of cell lysates, sample probing with antibodies, and analysis of RPPA were performed as described previously (Hennessy et al 2010).

Example 1

Ectopic Overexpression of HER2 Confers Autonomous Growth to Human Mammary Epithelial Cells Previous studies modeled DCIS by overexpressing fusion proteins, comprising HER2 (intracellular domain) and the ectodomain of the receptor for the nerve growth factor, in MCF10A immortalized human mammary cells (Debnath et al 2002, Muthuswamy et al 2001). To model the effects of wild type, full-length HER2 on DCIS, the present inventors constructed MCF10A cells ectopically overexpressing the oncoprotein (C-R. Pradeep et al., manuscript submitted). Briefly, cells were stably infected with retroviral particles encoding HER2 and IRES-GFP (hereafter denoted MCF10A-HER2 cells) or IRES-GFP alone (hereafter MCF10A; (Ueda et al, 2004)). Immunoblotting of cell lysates obtained after stimulation with EGF or with neuregulin (NRG1-beta), respectively, confirmed that HER2 enhanced and prolonged the activation of the ERK pathway, as well as delayed EGFR degradation (FIG. 1A) (Pinkas-Kramarski et al, 1996; Worthylake et al., 1999). These effects on signaling kinetics translated to enhanced cellular proliferation. Unlike MCF10A cells, whose proliferation rates depended on growth factors and reached saturation, the enhanced proliferation rates of MCF10A-HER2 cells were not affected by growth factors and showed no density-induced saturation (FIG. 1B). Thus, when overexpressed in normal mammary cells, HER2 confers autonomous cell growth, independent of growth factors.

Example 2

HER2 Transcriptionally Induces Multiple Components of the Notch Pathway

Figure 2B:
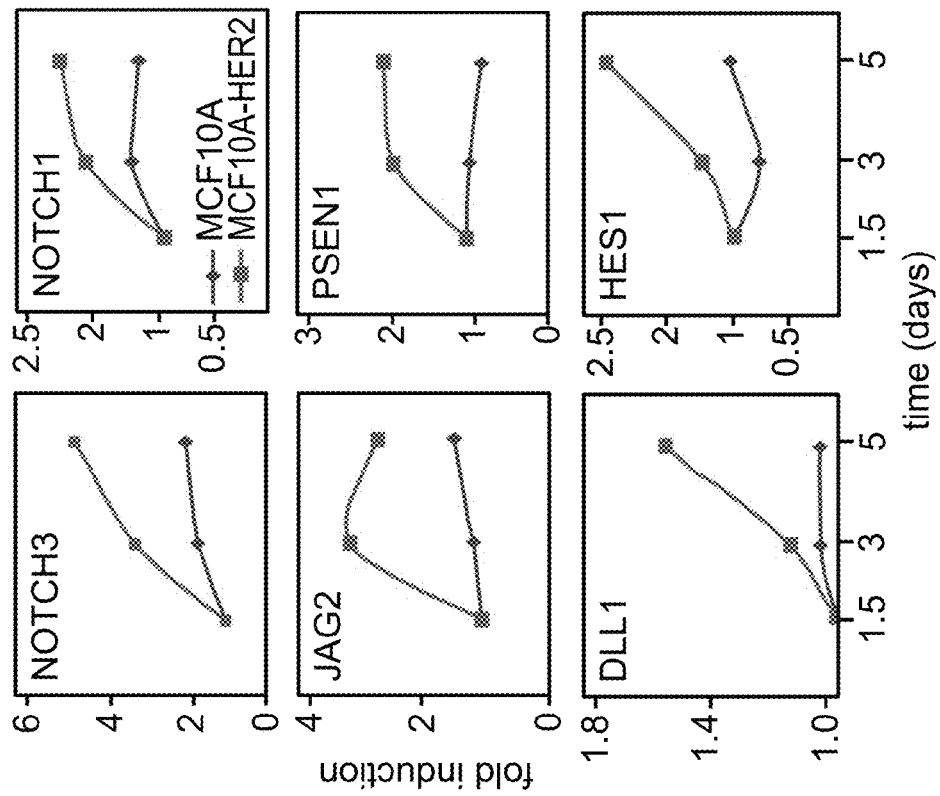
Figure 2A:
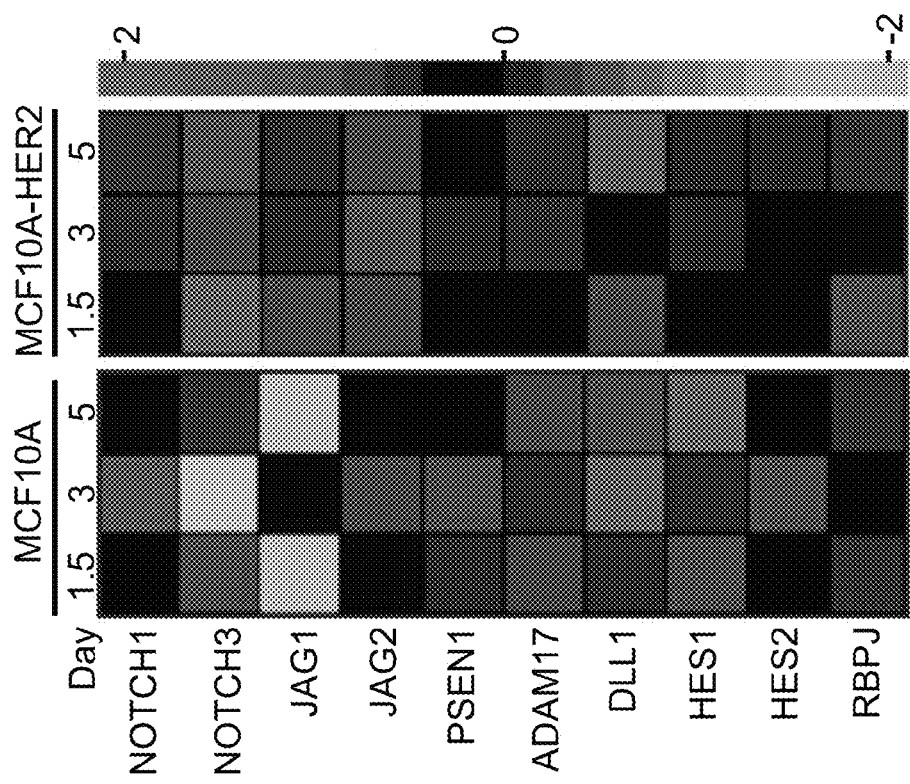
Figure 2C:
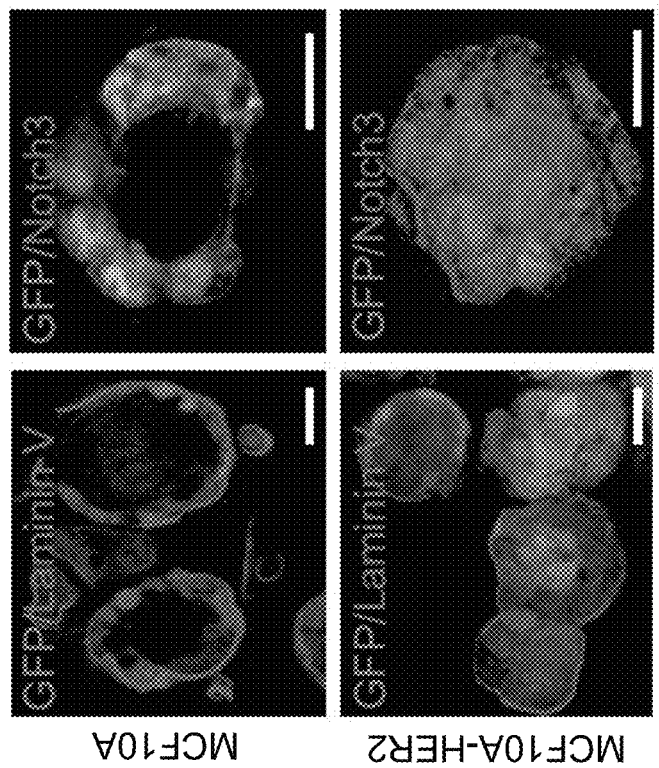

To resolve molecular bases underlying the growth autonomy conferred by HER2, the present inventors employed a three-dimensional (3D) culture system of MCF10A cells (reviewed in (Debnath and Brugge 2005)). When grown in a preparation of extracellular matrix (Matrigel™), these cells display clonal formation of hollow spheroids, which were reported to undergo luminal filling when an ectopically expressed chimeric HER2 was forced to form homodimers (Muthuswamy et al 2001). The present MCF10A-HER2 cells overexpressing wild type HER2 similarly exhibited luminal filling, even in the absence of further treatments. Notably the MCF10A-HER2 spheroids retained an intact outer structure without any evidence of invasion (data not shown and FIG. 2D, left panels). To identify the gene expression programs that promote luminal filling, RNA was extracted from 3D structures and hybridized to oligonucleotide microarrays. As expected, analyses of mRNAs significantly altered in MCF10A-HER2 cells revealed up-regulation of cell proliferation modules and downregulation of transcripts that belong to pro-apoptosis pathways. In addition, a persistent up-regulation of several components of the Notch pathway was noted, including two receptors and three JAG/DLL ligands, as well as ADAM17 and Presenilin1, proteases that cleave and activate Notch (FIG. 2A). Congruent with simultaneous, multi-site induction of the Notch pathway, two prototypic target genes of the pathway, HES1 and HES2, also displayed elevated expression. The transcriptional induction of several of these components was confirmed by using quantitative real-time PCR (qRT-PCR; FIG. 2B). Next, by applying a MEK-specific inhibitor (U0126) it was found that the MAPK-ERK pathway, the major downstream effector of HER2, contributes to the transcriptional induction of the Notch pathway in lumen-filled spheroids (FIG. 2C).

Figure 2D:
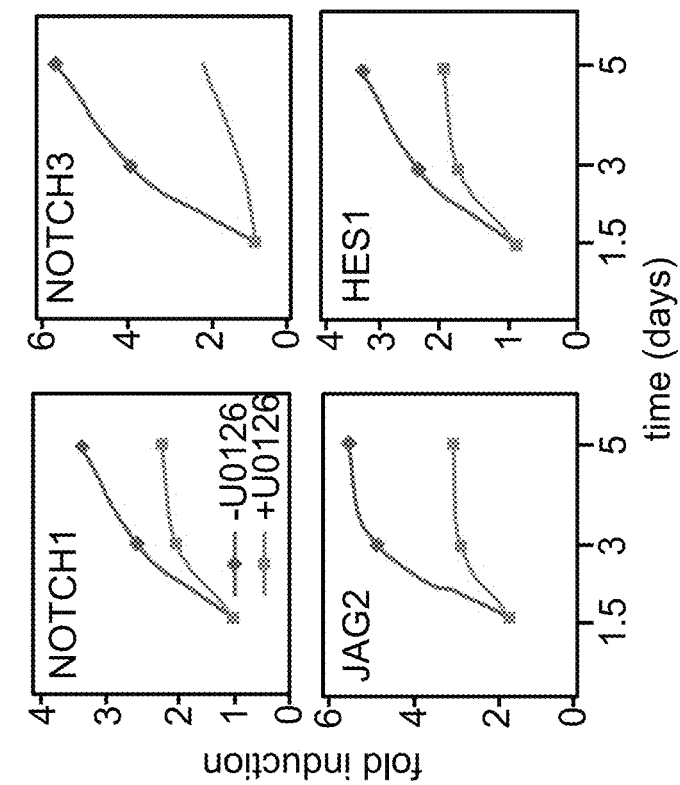
Figure 2F:
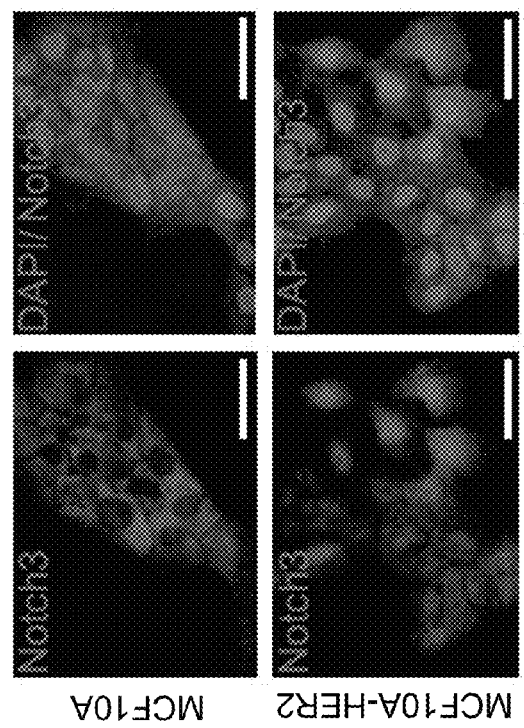

On losing contact with their extracellular matrix, luminal mammary cells, as well as MCF10A cells grown in spheroids, undergo anoikis, resulting in lumen formation, unless oncogenes like HER2, which enhances proliferation and inhibits apoptosis, are activated (Debnath et al 2002, Simpson et al 2008). Consistent with the possibility that the bypass of anoikis is mediated by the Notch pathway, it was found that MCF10A-HER2 cells strongly expressed Notch3, whereas the hollow spheroids formed by MCF10A cells exhibited relatively weak expression (FIG. 2D, right panels). Interestingly, both luminal and peripheral cells of MCF10A-HER2 spheroids immunostained positively for Notch3, but expression of the protein was accentuated in the core, especially along cell-to-cell contacts.

Figure 2E:
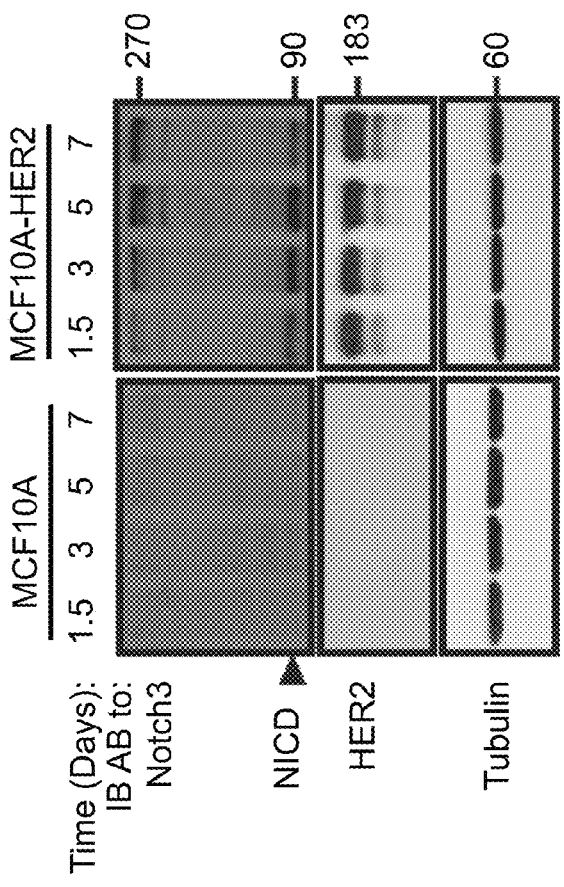

Western blotting of lysates from monolayers confirmed that Notch3 and its active cleavage product, NICD, were expressed at higher levels in MCF10A-HER2 cells compared to MCF10A cells (FIG. 2E). Interestingly, treatment with EGF elicited very small, if any, effects on both Notch3 expression and NICD levels, in line with requirement for and sufficiency of HER2 overexpression. Immunostaining of monolayers confirmed enhanced Notch3 expression in MCF10A-HER2 cells, along with punctate staining for Notch3 within nuclei (FIG. 2F, inset), suggestive of nuclear translocation of the NICD. Notably, unlike the observed localization of Notch3 to cell contacts of 3D structures, diffuse staining was observed in cell monolayers, which may relate to differences between monolayers and mammospheres and the disruptive effect of HER2 on epithelial polarity (Aranda et al 2006). In aggregate, HER2 overexpression leads to transcriptional induction of multiple components of the Notch survival pathway, raising the possibility that Notch3 mediates the effects of HER2 on luminal filling.

Example 3

Notch3 Promotes Survival and Proliferation of HER2-Overexpressing Cells

Figure 3C:
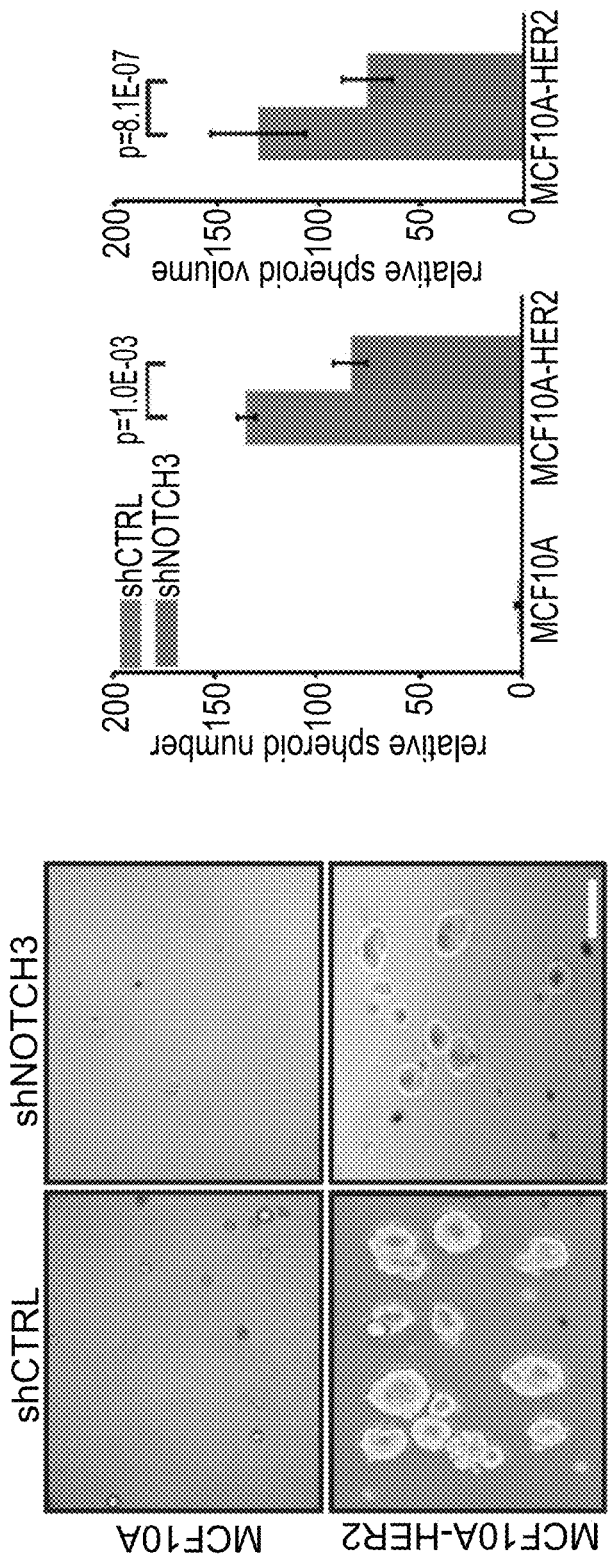

To test whether Notch3 is required for survival and proliferation, Notch3 expression was stably reduced by applying shRNA to MCF10A and MCF10A-HER2 cells (FIG. 3A). When analyzed in monolayers, Notch3 knockdown significantly decreased proliferation of MCF10A-HER2 cells, such that they displayed growth rates similar to MCF10A cells expressing control shRNA (FIG. 3B). Notably, manipulating Notch3 expression in the absence of HER2 overexpression did not affect growth rates, implying functional association between an overexpressed HER2 and Notch3. To analyze the effect of Notch3 knockdown in 3D cultures, two distinct approaches were applied. The first protocol, a suspension culture in the polyHEMA polymer (Dontu et al 2003), revealed that neither shControl- nor shNotch3-expressing MCF10A cells formed mammospheres. In agreement with the ability of HER2 to confer autonomous growth, MCF10A-HER2 cells readily formed multi-cell mammospheres, with Notch3 knockdown significantly reducing both the number and the size of mammospheres (FIG. 3C).

Figure 3D:
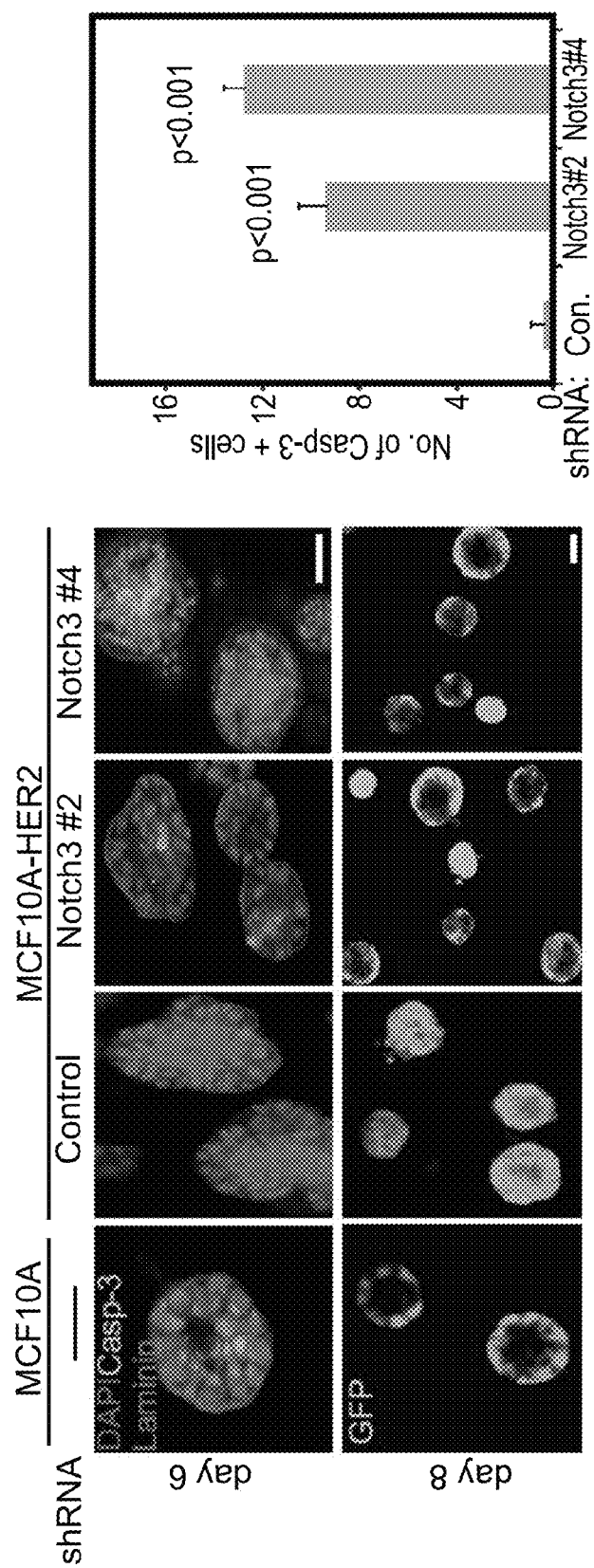

The second protocol, spheroids grown in Matrigel™, similarly reflected essential roles of Notch3. Unlike MCF10A cells, which developed hollow spheroids by day 8, HER2-overexpressing cells evolved lumen-filled spheroids. Notch3 knockdown largely reversed the HER2-induced phenotype, resulting in lumen formation (FIG. 3D). Staining of spheroids at day 6 for the active, cleaved form of Caspase-3 revealed luminal activity of this apoptosis-executing protease in MCF10A spheroids, as well as in Notch3 knocked-down MCF10A-HER2 spheroids, in line with the notion that the Notch pathway enables HER2-overexpressors to evade anoikis (FIG. 3D). In conclusion, three different culture approaches indicated that the Notch pathway underlies the effects of HER2 on enhanced growth and survival of mammary cells.

Example 4

Notch3-Induced c-Myc, Cyclin D and AKT Activity Underlie the Growth Promoting Effect of HER2

Figure 4B:
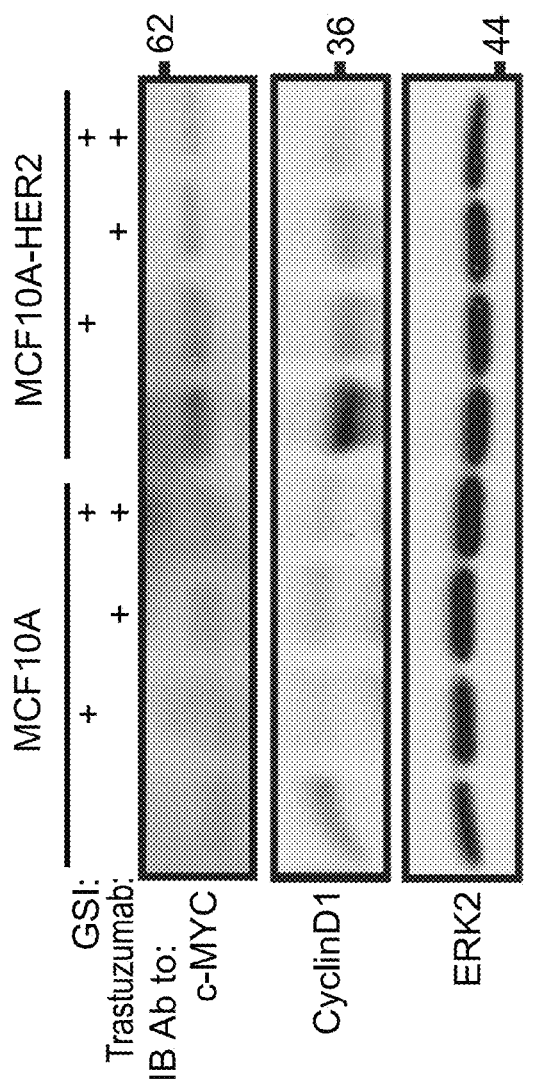
Figure 4A:
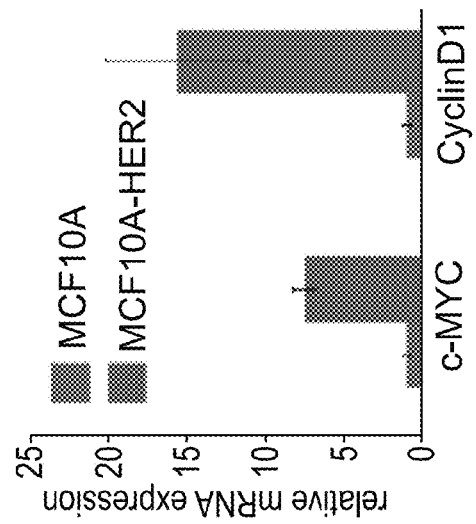

Previous studies implicated c-Myc and Cyclin D1 in Notch-induced growth and survival signals (Cohen et al 2010, Palomero et al 2006) Likewise, the present qRT-PCR analyses revealed a much higher expression of both c-Myc and Cyclin D1 in MCF10A-HER2 spheroids, relative to MCF10A spheroids (FIG. 4A), and immunoblotting confirmed these associations at the protein level (FIG. 4B). Inhibition of either HER2 signaling (using the monoclonal antibody Trastuzumab) or Notch signaling (using an inhibitor of γ-secretase; GSI) reduced c-c-Myc and Cyclin D1 protein levels, with maximal reduction occurring upon treatment with the combination of drugs (FIG. 4B). In the same vein, immunoblot analysis confirmed that knockdown of Notch3 in MCF10A-HER2 cells using shRNA decreased the expression of both Cyclin D1 and c-Myc (FIG. 4C).

To substantiate the conclusion that transcriptional induction of Notch3 and its regulated proteolytic cleavage suffice to induce Cyclin D1 and c-Myc, the present inventors ectopically expressed NICD in two non-HER2 overexpressing mammary epithelial cell lines, MDA-MB231 and MCF10A. As expected, this resulted in concomitant up-regulation of c-Myc and Cyclin D1 (FIG. 4D) (Palomero et al 2006). Next, by using siRNA oligonucleotides, the present inventors silenced the expression of the transcriptional repressor HES1, a well-established target of NICD, in two HER2 overexpressing lines, BT474 and MCF10A-HER2. HES1 knockdown enhanced the expression of the lipid phosphatase PTEN, in line with previous reports (Palomero et al 2007, Whelan et al 2007), and accordingly diminished the activating phosphorylation of AKT on serine-473 (FIG. 4E). Taken together, these results implicate up-regulation of c-Myc and Cyclin D1, along with enhanced activation of AKT phosphorylation, in a HER2-Notch survival pathway of mammary cells.

Figure 4F:
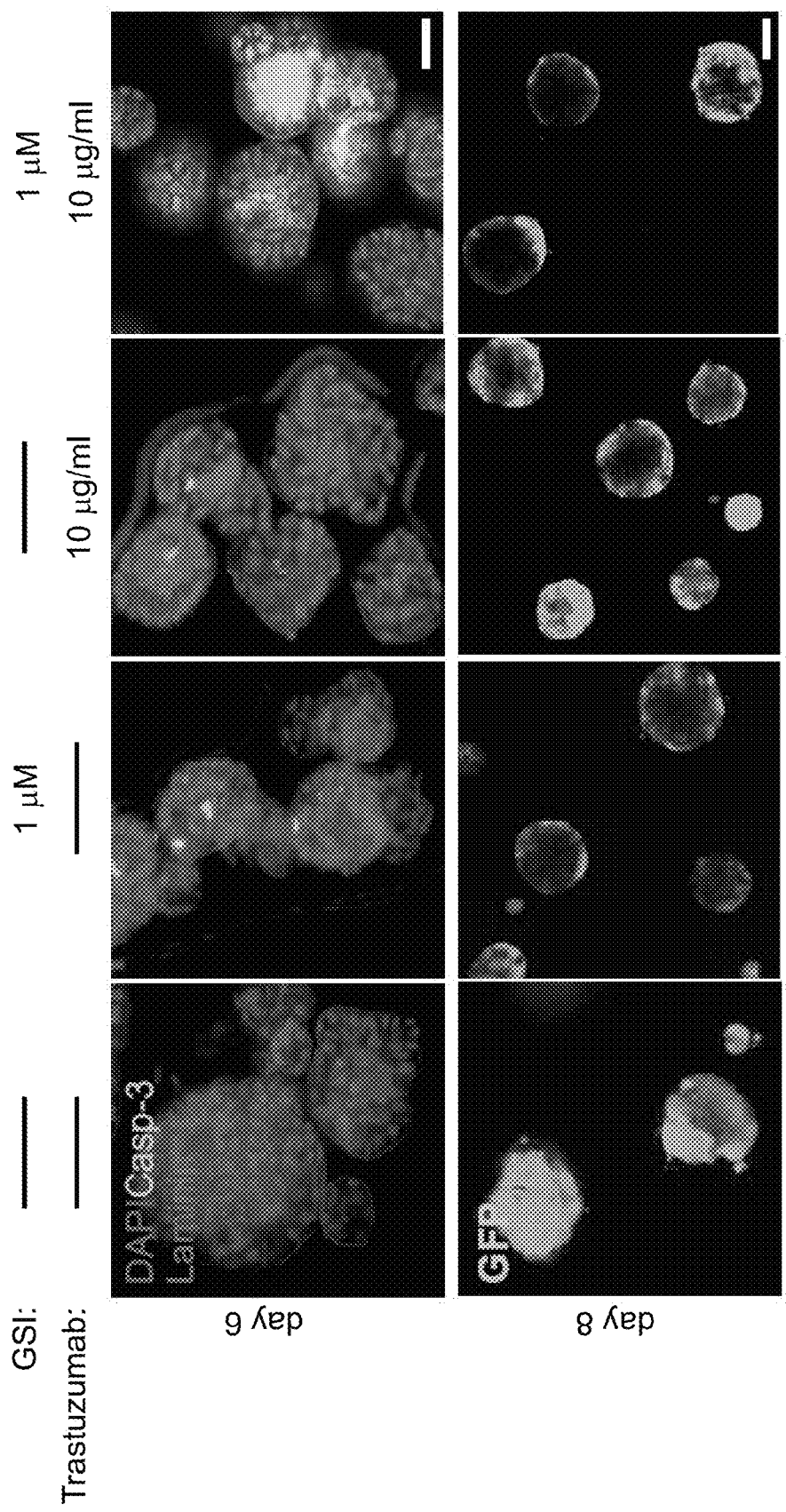
Figure 4G:
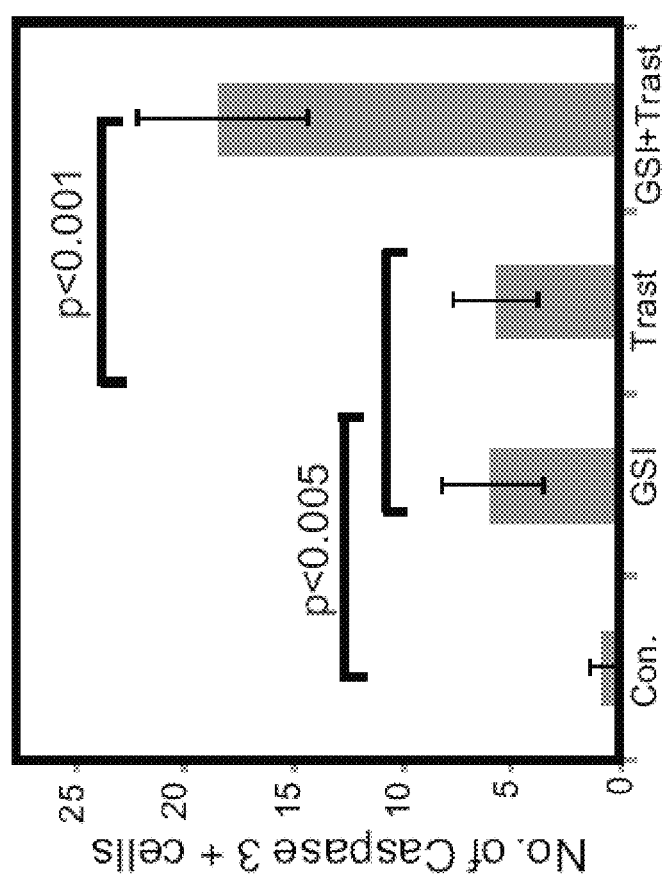

To explore phenotypic consequences of the collaboration between HER2 and Notch3, MCF10A-HER2 spheroids were cotreated with Trastuzumab and GSI. Whereas either drug alone enhanced apoptosis of luminal cells in MCF10A-HER2 spheroids, their combination almost completely abolished formation of filled lumina (FIG. 4F). Similarly, when applied on MCF10A-HER2 spheroids, pathway-specific inhibitors targeting MEK (U0126), c-Myc (10058-F4) or PI3K-AKT (LY-294002) markedly enhanced Caspase-3 activation, resulting in significant inhibition of luminal filling (FIG. 4G). In conclusion, the HER2-to-Notch axis is linked to an apoptosis evasion mechanism that entails c-Myc and Cyclin D1, along with coupling HER2 to AKT activation.

Example 5

Notch3 Expression Correlates with HER2 Levels in an Animal Model and in Human Breast Cancer Specimens Studies using transgenic mice demonstrated that overexpression of an activated form of Notch1 or Notch3 in the mammary gland results in increased formation of mammary tumors (Hu et al, 2006). The present results using 2D and 3D models of HER2-overexpressing DCIS propose that HER2 activation harnesses the Notch pathway to accelerate cellular proliferation, and hence may support mammary tumors in vivo. To test this prediction, the present inventors stained for Notch3 mammary glands of transgenic mice carrying an activated form of the HER2/neu oncogene, under the control of the mouse mammary tumor virus (MMTV) long terminal repeat (Bouchard et al 1989, Tekmal et al 2007).

Indeed, hyperplastic lesions, which frequently develop in the mammary glands of MMTV-HER2/neu transgenic mice, exhibited homogeneous weak to moderate immunohistochemical staining for Notch3, which was accentuated in cells facing the ductal lumen (FIG. 5A). Conversely, normal mammary glands of non-HER2 transgenic mice from the same strain displayed a heterogeneous staining pattern, with Notch3 expression mostly confined to small ducts (FIG. 5A), likely reflecting a role in the transition from small to mature ducts.

To determine the relevance of the present findings to human breast cancer, two clinical datasets were analyzed (Desmedt et al 2007, Schmidt et al 2008), each derived from oligonucleotide microarray analyses of approximately 200 breast cancer patients, for possible associations between HER2 mRNA expression and presence of components of the Notch pathway. In line with the present in vitro expression data (FIG. 2B), Notch3 along with presenilin and HES1 presented highly significant correlations with HER2 expression (Table 1). Interestingly, the present analyses found weak negative correlation between HER2 and Notch1, although co-expression of JAG-1 and Notch1 occurs in aggressive human breast tumors, which do not belong to the HER2 subtype (Reedijk et al 2005).

TABLE 1

| | Dataset (number of patients) | | | |
|---|---|---|---|---|
| | Desmedt et al., 2007 (n = 198) | | Schmidt et al., 2008 (n = 200) | |
| | Correlation coefficient (r) | p-value | Correlation coefficient (r) | p-value |
| NOTCH3 | 0.312 | 7.23E−06 | 0.257 | 2.36E−04 |
| PSEN1 | 0.355 | 2.67E−07 | 0.425 | 3.44E−10 |
| HES1 | 0.281 | 5.83E−05 | 0.309 | 6.30E−06 |
| NOTCH1 | −0.226 | 1.40E−03 | −0.249 | 3.80E−04 |
| NOTCH2 | −0.100 | 1.61E−01 | −0.306 | 1.03E−05 |

In order to confirm the association between HER2 and Notch3 at the protein level in clinical specimens, reverse-phase protein arrays (RPPA) were used (Hennessy et al 2010). Analyses of mammary tumors from two independent patient cohorts (approximately 100 patients per cohort) confirmed significant correlation between the phosphorylated, active form of HER2 (p1248HER2) and Notch3 (cohort 1: r=0.43, p=1.55E-05; cohort 2: r=0.23, p=2.58E-02; FIG. 5B). Moreover, in both data sets Notch3 protein levels also significantly correlated with EGFR expression (r=0.37 or 0.28; p<1.00E-02 for both). Individual patient-related data were available for the second cohort, for which subgroup analyses revealed correlation of Notch3 with levels of HER2 (r=0.31, p=3.16E-02) and p1248HER2 (r=0.34, p=1.80E-02) in 48 patients with poorly differentiated tumors. However, no such correlation was observed in moderately or well-differentiated tumors (HER2 r=0.03, p1248HER2 r=0.18, p>5.00E-02 for both). On the other hand, patient subgroups defined by age, menopausal status or expression of the estrogen receptor (ER) and/or the progesterone receptor (PR) did not exhibit differences with respect to the correlation between Notch3 and either HER2 or p1248HER2 (data not shown).

In summary, the present in vitro results, animal studies and clinical data lend collective support to an hypothesis arguing that the non-invasive cell proliferation associated with HER2-overexpressing mammary lesions, such as DCIS, is mediated, by the Notch pathway. Apparently, by activating proliferation and survival pathways comprising c-Myc, Cyclin D, and AKT, Notch signaling mediates filling of mammary ducts with HER2-overexpressing cells.

DISCUSSION

The evolutionary conserved Notch signaling pathway is considered a critical regulator of cell fate decisions in embryonic development, including hematopoiesis, neurogenesis and development of several organs, such as the mammary gland (Liu et al 2010). For example, proliferation and differentiation of mammary stem cells towards luminal and myoepithelial cell lineages are controlled in large part by the Notch pathway (Shackleton et al 2006, Stingl et al 2006). Thus, ectopic activation of Notch signaling commits mammary stem cells to the luminal lineage, as well as enhances proliferation of luminal cells, leading ultimately to their transformation (Bouras et al 2008). On the other hand, inhibition of Notch signaling enhances self-renewal, rather than differentiation, of mammary stem cells. It is, therefore, not surprising that the Notch pathway is amply employed by tumor cells to thrust their survival and growth. Whereas in small cell lung cancer, Notch may act as a tumor suppressive pathway (Sriuranpong et al 2001), gain-of-function mutations and a chromosomal translocation leading to constitutive activation of Notch1 were identified in human T-cell acute lymphoblastic leukemia (Ellisen et al 1991, Weng et al 2004), gene amplification of Notch3 was detected in ovarian cancer (Nakayama et al 2007), and relatively low levels of the Notch antagonist Numb were noted in breast tumors (Pece et al 2004). The present study unveils yet another mechanism that harnesses Notch signaling to promote malignant growth. Coordinated transcriptional induction of several Notch pathway components (summarized in FIG. 5C) appears essential for HER2-induced enhancement of proliferation and survival of mammary epithelial cells. Importantly, the 3D experimental model employed herein proposes that the HER2-to-Notch pathway, although robustly promoting growth factor-independent cell proliferation, is unable to induce basement membrane breakdown and subsequent invasive growth. Presumably, additional insults are needed to unleash the migratory potential of HER2-initiated cells. Interestingly, stimulation with EGF, which promotes formation of heterodimers of HER2 with the EGF-receptor, was reported to be sufficient for the emergence of an invasive phenotype of HER2-overexpressing spheroids (Zhan et al 2006).

Previous clinical and other lines of evidence are consistent with the present conclusion that HER2 overexpression in the mammary epithelium is functionally linked to the Notch pathway, and this interaction represents an early step in breast cancer development. For example, a recent study found that enhanced expression of Notch1 was an early event in both a murine model of DCIS and in human breast tumors, but Notch3 and other components were not analyzed (Zardawi et al 2010). Additionally, these authors reported an association between Notch1 and HER2 abundance, but high Notch1 was not prognostic. Interestingly, a positive feedback loop may escalate HER2 and Notch expression in tumors; transcription of HER2 was shown to be enhanced by Notch1 in a process involving PEA3. According to another report, Notch-mediated up-regulation of HER2 enhances the tumor-initiating potential of mammary cells (Clemenz and Osipo 2009). The present study reveals another bi-directional crosstalk that enables HER2 and Notch to collaboratively confer growth factor independence and populate the lumen of mammary ducts. Because HER2 cannot directly recruit PI3K, an enzyme required for survival signaling by the AKT pathway, it must engage a surrogate receptor, such as ERBB-3/HER3 (Prigent and Gullick 1994, Wallasch et al 1995). The results presented herein delineate an alternative mechanism, analogous to the mode identified in leukemia (Palomero et al 2008): Notch activation reduces PTEN expression, and thereby elevates levels of 3' phosphoinositides necessary for AKT stimulation.

Beyond the understanding that two oncogenic pathways, HER2 and Notch, jointly constitute a novel module that likely underlies the luminal filling characteristics of DCIS, the present study bears potential clinical implications. Two implications are worth mentioning, especially in light of the current debate pertaining to relative risks and optimal treatment of this non-invasive neoplasm. For one, co-incidence of HER2 and active Notch may identify a group of DCIS patients who are at increased risk of relapse after surgery. Secondly, the ongoing interactions between HER2 and Notch in later stages of tumor development, as pointed out in our study, highlight the potential of treatment strategies that combine anti-HER2 antibodies with Notch antagonists (such as GSI) or with PI3K/AKT kinase inhibitors. Such combinations displayed effectiveness in the present 3D model system, hence may prove useful in clinical settings.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Aranda V, Haire T, Nolan M E, Calarco J P, Rosenberg A Z, Fawcett J P et al (2006). Par6-aPKC uncouples ErbB2 induced disruption of polarized epithelial organization from proliferation control. *Nat Cell Biol* 8: 1235-1245.

Bouchard L, Lamarre L, Tremblay P J, Jolicoeur P (1989). Stochastic appearance of mammary tumors in transgenic mice carrying the MMTV/c-neu oncogene. *Cell* 57: 931-936.

Bouras T, Pal B, Vaillant F, Harburg G, Asselin-Labat M L, Oakes S R et al (2008). Notch signaling regulates mammary stem cell function and luminal cell-fate commitment. *Cell Stem Cell* 3: 429-441.

Clemenz A Z, Osipo C (2009). Notch1 activates ErbB-2 through a PEA3-dependent mechanism. *Cancer Research* 69: 362s.

Cohen B, Shimizu M, Izrailit J, Ng N F, Buchman Y, Pan J G et al (2010). Cyclin D1 is a direct target of JAG1-mediated Notch signaling in breast cancer. *Breast Cancer Res Treat* 123: 113-124.

Debnath J, Mills K R, Collins N L, Reginato M J, Muthuswamy S K, Brugge J S (2002). The role of apoptosis in creating and maintaining luminal space within normal and oncogene-expressing mammary acini. *Cell* 111: 29-40.

Debnath J, Walker S J, Brugge J S (2003). Akt activation disrupts mammary acinar architecture and enhances proliferation in an mTOR-dependent manner. *J Cell Biol* 163: 315-326.

Debnath J, Brugge J S (2005). Modelling glandular epithelial cancers in three-dimensional cultures. *Nat Rev Cancer* 5: 675-688.

Desmedt C, Piette F, Loi S, Wang Y, Lallemand F, Haibe-Kains B et al (2007). Strong time dependence of the 76-gene prognostic signature for node-negative breast cancer patients in the TRANSBIG multicenter independent validation series. *Clin Cancer Res* 13: 3207-3214.

Dontu G, Abdallah W M, Foley J M, Jackson K W, Clarke M F, Kawamura M J et al (2003). In vitro propagation and transcriptional profiling of human mammary stem/progenitor cells. *Genes Dev* 17: 1253-1270.

Ellisen L W, Bird J, West D C, Soreng A L, Reynolds T C, Smith S D et al (1991). TAN-1, the human homolog of the *Drosophila* notch gene, is broken by chromosomal translocations in T lymphoblastic neoplasms. *Cell* 66: 649-661.

Hennessy B, Lu Y, Gonzalez-Angulo A M, Myhre S, Carey M, Ju Z et al (2010). A technical assessment of the utility of reverse phase protein arrays for the study of the functional proteome in non-microdissected human breast cancers. *Clinical Proteomics*: in press.

Howlin J, McBryan J, Martin F (2006). Pubertal mammary gland development: insights from mouse models. *J Mammary Gland Biol Neoplasia* 11: 283-297.

Hudziak R M, Lewis G D, Winget M, Fendly B M, Shepard H M, Ullrich A (1989). p185HER2 monoclonal antibody has antiproliferative effects in vitro and sensitizes human breast tumor cells to tumor necrosis factor. *Mol Cell Biol* 9: 1165-1172.

Ignatiadis M, Desmedt C, Sotiriou C, de Azambuja E, Piccart M (2009). HER-2 as a target for breast cancer therapy. *Clin Cancer Res* 15: 1848-1852.

Imatani A, Callahan R (2000). Identification of a novel NOTCH-4/INT-3 RNA species encoding an activated gene product in certain human tumor cell lines. *Oncogene* 19: 223-231.

Iso T, Kedes L, Hamamori Y (2003). HES and HERP families: multiple effectors of the Notch signaling pathway. *J Cell Physiol* 194: 237-255.

Jechlinger M, Podsypanina K, Varmus H (2009). Regulation of transgenes in three-dimensional cultures of primary mouse mammary cells demonstrates oncogene dependence and identifies cells that survive deinduction. *Genes Dev* 23: 1677-1688.

Katz M, Amit I, Citri A, Shay T, Carvalho S, Lavi S et al (2007). A reciprocal tensin-3-cten switch mediates EGF-driven mammary cell migration. *Nat Cell Biol* 9: 961-969.

Liu J, Sato C, Cerletti M, Wagers A (2010). Notch signaling in the regulation of stem cell self-renewal and differentiation. *Curr Top Dev Biol* 92: 367-409.

Lonardo F, Di Marco E, King C R, Pierce J H, Segatto O, Aaronson S A et al (1990). The normal erbB-2 product is an atypical receptor-like tyrosine kinase with constitutive activity in the absence of ligand. *New Biol* 2: 992-1003.

Muthuswamy S K, Li D, Lelievre S, Bissell M J, Brugge J S (2001). ErbB2, but not ErbB1, reinitiates proliferation and induces luminal repopulation in epithelial acini. *Nat Cell Biol* 3: 785-792.

Nakayama K, Nakayama N, Jinawath N, Salani R, Kurman R J, Shih Ie M et al (2007). Amplicon profiles in ovarian serous carcinomas. *Int J Cancer* 120: 2613-2617.

Palomero T, Lim W K, Odom D T, Sulis M L, Real P J, Margolin A et al (2006). NOTCH1 directly regulates c-MYC and activates a feed-forward-loop transcriptional network promoting leukemic cell growth. *Proc Natl Acad Sci USA* 103: 18261-18266.

Palomero T, Sulis M L, Cortina M, Real P J, Barnes K, Ciofani M et al (2007). Mutational loss of PTEN induces resistance to NOTCH1 inhibition in T-cell leukemia. *Nat Med* 13: 1203-1210.

Palomero T, Dominguez M, Ferrando A A (2008). The role of the PTEN/AKT Pathway in NOTCH1-induced leukemia. *Cell Cycle* 7: 965-970.

Pece S, Serresi M, Santolini E, Capra M, Hulleman E, Galimberti V et al (2004). Loss of negative regulation by Numb over Notch is relevant to human breast carcinogenesis. *J Cell Biol* 167: 215-221.

Perou C M, Sorlie T, Eisen M B, van de Rijn M, Jeffrey S S, Rees C A et al (2000). Molecular portraits of human breast tumours. *Nature* 406: 747-752.

Prigent S A, Gullick W J (1994). Identification of c-erbB-3 binding sites for phosphatidylinositol 3'-kinase and SHC using an EGF receptor/c-erbB-3 chimera. *EMBO J* 13: 2831-2841.

Reedijk M, Odorcic S, Chang L, Zhang H, Miller N, McCready D R et al (2005). High-level coexpression of JAG1 and NOTCH1 is observed in human breast cancer and is associated with poor overall survival. *Cancer Res* 65: 8530-8537.

Schafer Z T, Grassian A R, Song L, Jiang Z, Gerhart-Hines Z, Irie H Y et al (2009). Antioxidant and oncogene rescue of metabolic defects caused by loss of matrix attachment. *Nature* 461: 109-113.

Schmidt M, Bohm D, von Torne C, Steiner E, Puhl A, Pilch H et al (2008). The humoral immune system has a key prognostic impact in node-negative breast cancer. *Cancer Res* 68: 5405-5413.

Shackleton M, Vaillant F, Simpson K J, Stingl J, Smyth G K, Asselin-Labat M L et al (2006). Generation of a functional mammary gland from a single stem cell. *Nature* 439: 84-88.

Simpson C D, Anyiwe K, Schimmer A D (2008). Anoikis resistance and tumor metastasis. *Cancer Lett* 272: 177-185.

Slamon D J, Clark G M, Wong S G, Levin W J, Ullrich A, McGuire W L (1987). Human breast cancer: correlation of relapse and survival with amplification of the HER-2/neu oncogene. *Science* 235: 177-182.

Slamon D J, Leyland-Jones B, Shak S, Fuchs H, Paton V, Bajamonde A et al (2001). Use of chemotherapy plus a monoclonal antibody against HER2 for metastatic breast cancer that overexpresses HER2. *N Engl J Med* 344: 783-792.

Sriuranpong V, Borges M W, Ravi R K, Arnold D R, Nelkin B D, Baylin S B et al (2001). Notch signaling induces cell cycle arrest in small cell lung cancer cells. *Cancer Res* 61: 3200-3205.

Stingl J, Eirew P, Ricketson I, Shackleton M, Vaillant F, Choi D et al (2006). Purification and unique properties of mammary epithelial stem cells. *Nature* 439: 993-997.

Stylianou S, Clarke R B, Brennan K (2006). Aberrant activation of notch signaling in human breast cancer. *Cancer Res* 66: 1517-1525.

Tekmal R R, Nair H B, Perla R P, Kirma N (2007). HER-2/neu×aromatase double transgenic mice model: the effects of aromatase overexpression on mammary tumorigenesis. *J Steroid Biochem Mol Biol* 106: 111-118.

van de Vijver M J, Peterse J L, Mooi W J, Wisman P, Lomans J, Dalesio O et al (1988). Neu-protein overexpression in breast cancer. Association with comedo-type ductal carcinoma in situ and limited prognostic value in stage II breast cancer. *N Engl J Med* 319: 1239-1245.

Wallasch C, Weiss F U, Niederfellner G, Jallal B, Issing W, Ullrich A (1995). Heregulin-dependent regulation of HER2/neu oncogenic signaling by heterodimerization with HER3. *EMBO J* 14: 4267-4275.

Weng A P, Ferrando A A, Lee W, Morris J Pt, Silverman L B, Sanchez-Irizarry C et al (2004). Activating mutations of NOTCH1 in human T cell acute lymphoblastic leukemia. *Science* 306: 269-271.

Whelan J T, Forbes S L, Bertrand F E (2007). CBF-1 (RBP-J kappa) binds to the PTEN promoter and regulates PTEN gene expression. *Cell Cycle* 6: 80-84.

Yarden Y, Sliwkowski M X (2001). Untangling the ErbB signalling network. *Nat Rev Mol Cell Biol* 2: 127-137.

Yin L, Velazquez O C, Liu Z J (2010). Notch signaling: emerging molecular targets for cancer therapy. *Biochem Pharmacol* 80: 690-701.

Zardawi S J, Zardawi I, McNeil C M, Millar E K, McLeod D, Morey A L et al (2010). High Notch1 protein expression is an early event in breast cancer development and is associated with the HER-2 molecular subtype. *Histopathology* 56: 286-296.

Zhan L, Xiang B, Muthuswamy S K (2006). Controlled activation of ErbB1/ErbB2 heterodimers promote invasion of three-dimensional organized epithelia in an ErbB1-dependent manner: implications for progression of ErbB2-overexpressing tumors. *Cancer Res* 66: 5201-5208.

administering to the subject a therapeutically effective amount of a first agent capable of down-regulating activity and/or expression of at least one component participating in a NOTCH pathway, and a second agent capable of down-regulating an activity and/or expression of HER2, wherein said second agent is an antibody, thereby treating the DCIS lesion.

2. The method of claim 1, further comprising analyzing in a breast sample of said subject an expression of said at least one component participating in a NOTCH pathway, prior to said treating.

3. The method of claim 2, further comprising analyzing in a breast sample of said subject an expression of HER2 prior to said treating.

4. The method of claim 1, further comprising analyzing in a breast sample of said subject an expression of HER2 prior to said treating.

5. The method of claim 1, wherein said antibody comprises Trastuzumab.

6. The method of claim 1, wherein said at least one component is selected from the group consisting of Hairy and Enhancer of Split 1(HES1), NOTCH 2, NOTCH 3, ADAM17 and Presenilin1.

7. The method of claim 1, wherein said at least one component is NOTCH3.

8. The method of claim 1, wherein said first agent is an siRNA molecule.

9. The method of claim 1, wherein said first agent is a gamma secretase inhibitor, a mitogen-activated protein kinase (MEK) specific inhibitor or a PI3K-AKT inhibitor.

10. The method of claim 9, wherein said first agent is a gamma secretase inhibitor.

11. A method of treating a ductal carcinoma in situ (DCIS) lesion in a subject in need thereof, the method comprising administering to the subject a therapeutically effective amount of a first agent selected from the group consisting of an antibody, an RNA silencing agent and an antagonist molecule capable of down-regulating activity and/or expression of at least one component participating in a NOTCH pathway

What is claimed is:

1. A method of treating a ductal carcinoma in situ (DCIS) lesion in a subject in need thereof, the method comprising selected from the group consisting of a NOTCH receptor, NOTCH ligand, NOTCH receptor intracellular domain (NICD), ADM17, presenilinl, HES, HERP, HEY, RBPSUH, Su(H), Lag-1, c-Myc and Cyclin D1, gamma-secretase, mitogen-activated protein kinase (MEK) and PI3K-AKT, and a second agent selected from the group consisting of an antibody, an RNA silencing agent and a kinase inhibitor molecule capable of down-regulating an activity and/or expression of HER2, thereby treating the DCIS lesion.

12. The method of claim 11, further comprising analyzing in a breast sample of said subject an expression of said at least one component participating in a NOTCH pathway, prior to said treating.

13. The method of claim 12, further comprising analyzing in a breast sample of said subject an expression of HER2 prior to said treating.

14. The method of claim 11, further comprising analyzing in a breast sample of said subject an expression of HER2 prior to said treating.

15. The method of claim 11, wherein said second agent is an antibody.

16. The method of claim 15, wherein said antibody comprises Trastuzumab.

17. The method of claim 11, wherein said second agent is a kinase inhibitor.

18. The method of claim 17, wherein said kinase inhibitor is lapatinib.

19. The method of claim 11, wherein said at least one component is selected from the group consisting of Hairy and Enhancer of Split 1 (HES1), NOTCH 2, NOTCH 3, ADAM17 and Presenilin1.

20. The method of claim 11, wherein said at least one component is NOTCH3.

21. The method of claim 11, wherein said first agent is an siRNA molecule.

22. The method of claim 11, wherein said first agent is a gamma secretase inhibitor, a mitogen-activated protein kinase (MEK) specific inhibitor or a PI3K-AKT inhibitor.

23. The method of claim 11, wherein said first agent is a gamma secretase inhibitor.

* * * * *